US012424026B1

(12) United States Patent
Alman

(10) Patent No.: US 12,424,026 B1
(45) Date of Patent: Sep. 23, 2025

(54) HANDHELD STRESS DEVICES AND METHODS FOR STRESS DETECTION AND MITIGATION

(71) Applicant: Brian Alman, Del Mar, CA (US)

(72) Inventor: Brian Alman, Del Mar, CA (US)

( * ) Notice: Subject to any disclaimer, the term of this patent is extended or adjusted under 35 U.S.C. 154(b) by 0 days.

(21) Appl. No.: 17/584,369

(22) Filed: Jan. 25, 2022

(51) Int. Cl.

| | |
|---|---|
| ***G06K 9/62*** | (2022.01) |
| ***A61B 5/16*** | (2006.01) |
| ***A61M 21/02*** | (2006.01) |
| ***G06T 7/00*** | (2017.01) |
| ***G06V 10/22*** | (2022.01) |
| ***G06V 10/25*** | (2022.01) |
| ***G06V 40/20*** | (2022.01) |
| ***G16H 20/70*** | (2018.01) |
| *A61M 21/00* | (2006.01) |

(52) U.S. Cl.

CPC .............. *G06V 40/20* (2022.01); *A61B 5/165* (2013.01); *A61M 21/02* (2013.01); *G06T 7/0012* (2013.01); *G06V 10/22* (2022.01); *G06V 10/25* (2022.01); *G16H 20/70* (2018.01); *A61M 2021/0027* (2013.01); *A61M 2021/0044* (2013.01); *A61M 2021/005* (2013.01); *G06T 2207/30088* (2013.01); *G06T 2207/30196* (2013.01)

(58) Field of Classification Search

CPC ........ G06V 40/20; G06V 10/22; G06V 10/25; G16H 20/70; A61B 5/165; A61M 21/02; A61M 2021/0027; A61M 2021/0044; A61M 2021/005; G06T 7/0012; G06T 2207/30088; G06T 2207/30196

USPC ........................................................... 348/77

See application file for complete search history.

(56) References Cited

U.S. PATENT DOCUMENTS

| | | | | |
|---|---|---|---|---|
| 10,237,304 | B1 * | 3/2019 | Sokolov | G06F 3/013 |
| 2018/0107962 | A1 * | 4/2018 | Lundin | G06Q 10/06398 |
| 2018/0255167 | A1 * | 9/2018 | Saito | G16H 30/40 |
| 2022/0027783 | A1 * | 1/2022 | Neumann | G16H 10/60 |
| 2023/0255531 | A1 * | 8/2023 | Tsujikawa | G16H 50/30 600/300 |

OTHER PUBLICATIONS

Oviyaa et al., Jul. 17, 2020, Real Time Tracking of Heart Rate from Facial Video Using Webcam, 2020 Second International Conference on Inventive Research in Computing Applications (ICIRCA), IEE https://ieeexplore.ieee.org/document/9183124?source=IQplus (Year: 2020).*

* cited by examiner

*Primary Examiner* — Jayanti K Patel

(74) *Attorney, Agent, or Firm* — Adibi IP Group, PC; Kian A. Tanner; Amir V. Adibi

(57) ABSTRACT

Stress assessment devices and methods are disclosed. In one embodiment, a method includes acquiring an image of a user, recognizing a region of interest (ROI) in the image, analyzing the ROI to generate statistics, and determining a level of stress experienced by the user based on the statistics. In one embodiment, an apparatus includes an image sensor that acquires an image of a user and a processor configured to perform operations that include recognizing a region of interest (ROI) in the image, analyzing the ROI to generate statistics, and determining a level of stress experienced by the user based on the statistics.

18 Claims, 20 Drawing Sheets

300
STRESS ASSESSMENT SYSTEM
302 PROCESS IMAGES, DATA, AND USER INPUT
304 MAINTAIN CURRENT HEALTH RECORDS
306 PROVIDE RESOURCES LIKE VIDEOS AND BLOGS
308 SYSTEM SETTINGS
310 ACCESS MITIGATION DATABASE
STRESS SCORE
312 RECOMMEND ACTIVITIES AND INTERVENTIONS
UPDATE MITIGATION DATABASE WITH EFFECTIVENESS RATINGS
314 PROVIDE ACCESS TO COUNSELORS AND PHYSICIANS
316 REDUCED STRESS LEVEL

| STRESS SCORE | MITIGATION STRATEGY | EFF. |
|---|---|---|
| 100 | (1) DEEP BREATHING | 8 |
| 150 | (1) DEEP BREATHING<br>(2) RELAXING MUSIC | 5<br>7 |
| 200 | (1) DEEP BREATHING<br>(2) RELAXING MUSIC<br>(3) MEDITATION | 3<br>---<br>8 |
| 250 | (1) RELAXING VIDEO<br>(2) COUNSELOR | 6<br>9 |

MITIGATION DATABASE

HANDHELD STRESS DEVICES AND METHODS FOR STRESS DETECTION AND MITIGATION

TECHNICAL FIELD

The present invention relates to portable, wireless stress-assessment devices, and more particularly to a portable wireless device configured to detect psychological stress and recommend treatment options.

BACKGROUND INFORMATION

Information can lead to knowledge, and actionable information can lead to change. It is now easy to collect, measure, and track all kinds of information, including health data. For example, in the comfort of one's own home it is now possible to monitor one's weight, blood pressure, heart rate, steps walked, calories burned, blood sugar, etc. Even so, objectively monitoring one's stress level has remained a significant challenge.

Psychological stress has been associated with many major chronic health disorders and cardiovascular diseases, and detecting whether a subject is suffering from psychological stress can assist in stress management, which can be important in maintaining a low stress level. It is generally appreciated that there are two types of psychological stress: acute stress and chronic stress. Acute stress is characterized by rapid changes in the autonomic nervous system, which is involved in the body's "fight or flight" responses to external stimuli. In contrast, chronic stress is characterized by prolonged exposure to stressful stimuli, which can cause long-term sympathetic hyperactivity.

Given the significant negative impacts psychological stress has on human health, there remains a longstanding need for devices that can easily and efficiently detect such stress and recommend treatment options.

SUMMARY

In various exemplary embodiments, handheld, wireless, stress assessment devices and methods are disclosed. In one embodiment, a user device, such as a portable, easy-to-use, wireless device, is configured to detect user stress and recommend treatment options. For example, such a device can be used by people during their daily lives, outside of a clinical setting, to easily and efficiently assess in real-time whether they are experiencing psychological stress, particularly acute psychological stress. Related objects of the invention concern systems that utilize such devices not only to provide such monitoring but also to suggest and make available one or more interventions intended to alleviate psychological stress.

Thus, in one aspect the embodiments concern portable, preferably wireless, stress assessment devices. Such devices will typically be handheld, and include smartphones, laptop computers, tablet computers, and the like. Such devices include a camera, preferably a forward facing video camera, and can run a computer program (or "application" or "app") to configure the device to determine, optionally in real-time and on-demand, if a subject is experiencing psychological stress. Such assessments are made by analyzing one or more parameters associated with blood flow through one or more tissue regions that can be imaged by the device's camera. Preferred examples of such parameters include heart rate (HR) and heart rate variability (HRV).

In preferred embodiments, devices constructed according to the embodiments are configured to acquire, analyze, process, store, and/or transmit data generated during or after a stress assessment. In preferred embodiments, the devices are configured to generate an output, preferably an output that is discernible to the user and/or one or more third parties, to indicate whether psychological stress has been detected. Such output includes audio output, haptic output, visual output, as well as various combinations of such outputs, for example, audio and visual outputs, haptic and visual outputs, and audio, haptic, and visual outputs.

In preferred embodiments, the output indicates whether psychological stress has been detected and this output is used to determine a methodology to provide one or more interventions designed to alleviate psychological stress.

In one embodiment, a method is provided that includes acquiring an image of a user, recognizing a region of interest (ROI) in the image, analyzing the ROI to generate statistics, and determining a level of stress experienced by the user based on the statistics.

In one embodiment, an apparatus is provided that includes an image sensor that acquires an image of a user and a processor configured to perform operations that include recognizing a region of interest (ROI) in the image, analyzing the ROI to generate statistics, and determining a level of stress experienced by the user based on the statistics.

Further details, embodiments, and methods are described in the detailed description below. This summary does not purport to define the invention. The invention is defined by the claims.

BRIEF DESCRIPTION OF THE DRAWINGS

The accompanying drawings, where like numerals indicate like components, illustrate embodiments of the invention.

DETAILED DESCRIPTION

Figure 1:
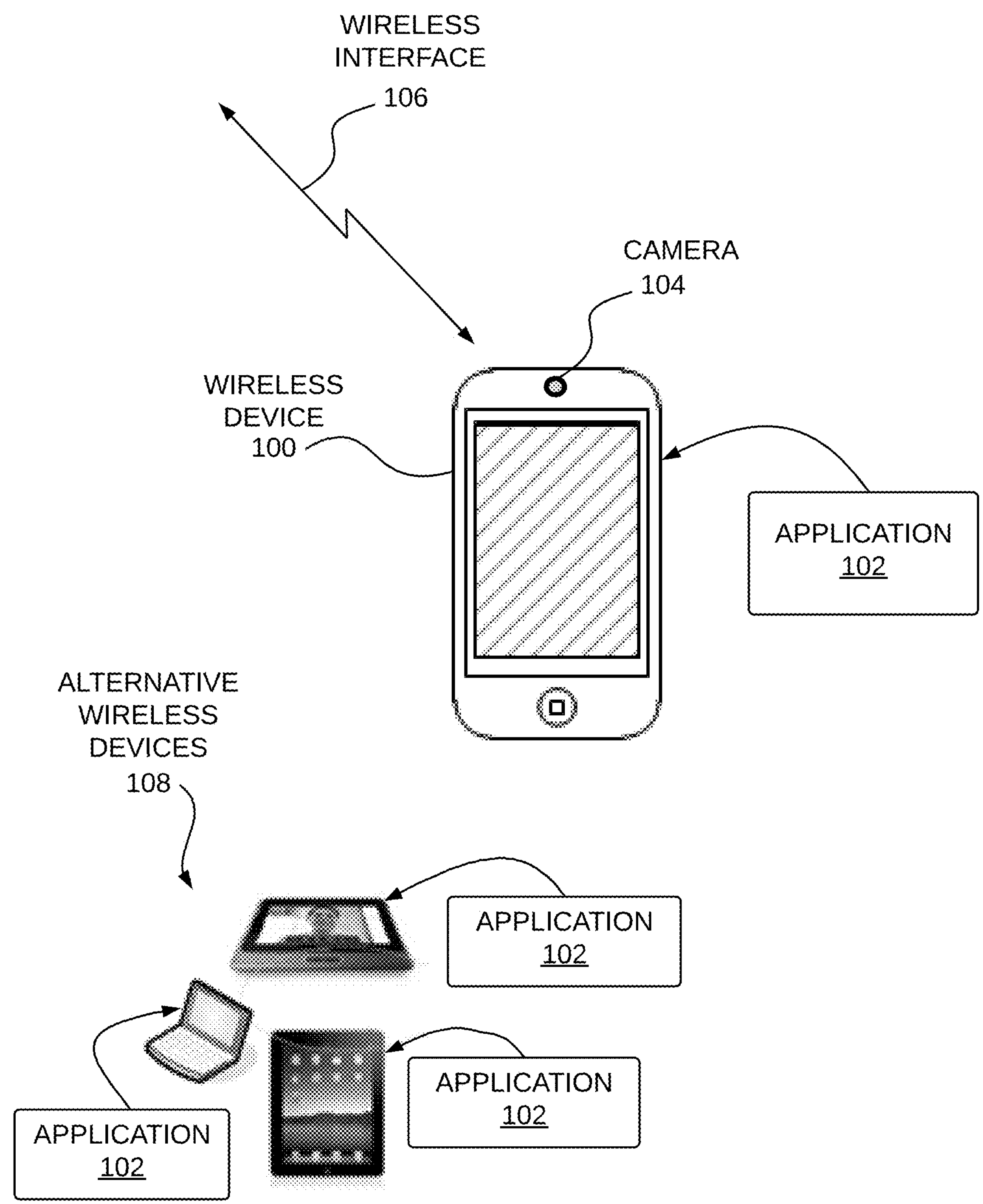
FIG. 1 shows an exemplary device configured to provide a real-time stress assessment system in accordance with various embodiments.

The present invention relates to portable, easy-to-use, wireless devices that can be used by people during their daily lives, outside of a clinical setting, to easily and efficiently assess in real-time whether they are experiencing psychological stress, particularly acute psychological stress.

In various exemplary embodiments, several terms used in the context of the embodiments are defined below. In addition to these terms, others are defined elsewhere in the specification, as necessary.

As used herein, the singular forms "a", "an", and "the" include plural references unless the context clearly dictates otherwise.

The term "about" refers to approximately a +/−10% variation from the stated value. It is to be understood that such a variation is always included in any given value provided herein, whether or not it is specifically referred to.

The term "and/or", when used in conjunction with two terms, e.g., A and/or B, means A or B or A and B. When the term is used in a string, e.g., A and/or B, and/or B and C, it means A or B or C, A and B, A and C, B and C, and A, B, and C, and so on for longer strings. Likewise, when a range of values us presented, e.g., 1-10, that range will be understood to include any and all specific values within that range, for example, 3.75 and 7 in the noted 1-10 range, and well as any sub-range, or series of smaller ranges, within the larger range.

An "app" refers to a computer program or application that runs, in whole or in part, on a computing device, e.g., a smartphone (e.g., an Iphone®), laptop computer, tablet computer (e.g., an iPad®, Chromebook®, etc.), etc. In some cases, an application runs in part on a mobile computing device and in part on another computer or computer network (e.g., a cloud based computer network) linked thereto, for example, via the Internet, be it via a hardwire (e.g., Ethernet) connection or wirelessly.

The terms "cloud computing", "cloud-based", "in the cloud", etc. refer to a computing model where services are delivered and used over the Internet on an as-needed basis, relying on shared computing resources rather than local servers or personal computing devices to run applications.

"Heart rate variability" or "HRV" refers to the variation in the heartbeat-to-heartbeat interval. It is also known in the art as "R-R variability" and "heart period variability". R-R variability refers to the interval corresponding to the R-R periods of the QRS complex. Heart rate variability, however, can also be represented by measuring the intervals between other repeating features of heartbeats, including various statistical measures derived from raw heartbeat-to-heartbeat interval data, such as variance and standard deviation.

The terms "measure", "measuring", "measurement", and the like refer not only to quantitative measurement of a particular variable but also to qualitative and semi-quantitative measurements. Accordingly, "measurement" also includes detection, meaning that merely detecting a change, without quantification, constitutes measurement.

The term "operably associated" refers to an operable association between two or more components.

A "plurality" means more than one.

A "subject" refers to a human subject.

"Test conditions" refers to the environmental conditions present during a particular test, be it a stress assessment test or a reference test to establish a pupil size reference under relaxed, non-stressed, preferably steady-state conditions. Such environmental conditions include parameters such as lighting intensity, spectral distribution, light source(s) (for example, artificial illumination, natural light (such as direct or indirect sunlight), or a combination of artificial and natural light), temperature, body position, etc. While it is preferred that as many parameters as possible are the same or substantially similar between stress assessment and reference testing, it is not essential, particularly when reference testing involves determining pupil size over a range of different environmental conditions (e.g., different lighting intensities).

The following description is presented to enable one of ordinary skills in the art to make and use embodiments of the invention. Various modifications to the preferred embodiment and the generic principles and features described herein will be readily apparent to those skilled in the art. Thus, the embodiments are not intended to be limited to those shown but are to be accorded the widest scope consistent with the principles and features described herein.

Aspects of Stress

The human body regulates its internal environment by various physiological processes, and maintains a state of equilibrium called homeostasis. Stress is the disruption of homeostasis and leads to a perturbed state of the human body. Stress can be triggered by various factors known as stressors. Stressors include physical (e.g., diseases/illness, allergy, fatigue, and poor sleep), psychological (e.g., conflicts, trauma, financial state, and work/educational demands), and environmental (e.g., noise, crowd, disasters, and pollution) influences. The human body's reaction to stressors is called a stress response, which is predominantly regulated by hypothalamic-pituitary-adrenocortical (HPA) and sympathetic-adrenal-medullary (SAM) systems. These systems interact by releasing stress hormones (glucocorticoids and catecholamines), and cause physiological changes related to vasomotor tones, heart rate (HR), heart rate variability (HRV), blood pressure (BP), and sweat production.

Psychological stress can be helpful in managing the demands of career, family, school, and work, accomplishing goals and tasks, and generating fight-or-flight responses during times of danger. On the other hand, psychological stress is one of the leading causes of major chronic health disorders, including diabetes, obesity, heart disease, gastrointestinal conditions, depression, and anxiety problems. As a result, psychological stress management is essential to maintain a low stress level, and thereby reduce health risks. Psychological stress levels are generally assessed based on self-assessment using questionnaires (e.g., State-Trait Anxiety Inventory (STAI)) and the perceived stress scale. Self-assessment is highly impractical over time, and it is also less reliable due to bias, subjectivity, random responding, and social compulsion to falsify the questionnaire responses to project a positive self-image.

When left untreated, acute and chronic psychological stress leads to a variety of health related challenges. Acute psychological stress results in a "fight or flight" response to external stimuli. This response creates a short-term increase in sympathetic tone and a decrease in parasympathetic tone, as well as increased heart rate (HR), increased low frequency heart rate variability (HRV), decreased high frequency HRV, and a decreased galvanic skin response (GSR). In contrast, chronic psychological stress is known to cause long-term sympathetic hyperactivity, as well as increased baseline cortisol production, increased sympathetic activation, increased blood pressure, blood vessel narrowing, decreased HRV, changes in HR, decreased physiological response to acute stress, and decreased baroreflex sensitivity. Thus, the balance between the sympathetic and parasympathetic components of the autonomic nervous system can be disrupted by such factors as psychological stress, which can cause the balance to shift toward the sympathetic, "fight-or-flight" response. If a person's system is in more of a fight-or-flight mode, the variation between heartbeats is low, whereas if a subject is in a more relaxed state, the variation between heartbeats is high. Research has shown a relationship between low HRV and worsening depression or anxiety. It has also been associated with an increased risk of death and cardiovascular disease. In contrast, a high HRV correlates with greater cardiovascular fitness and resilience to psychological stress.

The various embodiments capitalize on the body's responses, particularly vascular responses (e.g., in terms of heart rate (HR), heart rate variability (HRV), blood pressure (BP), blood vessel size, etc.) to psychological stress by providing portable wireless devices, preferably small, nearly ubiquitous handheld devices, such as smartphones, to measure one or more blood flow parameters associated or correlated with psychological stress in order to determine if someone is experiencing such stress, particularly acute psychological stress.

FIG. 1 shows an exemplary device 100 configured to provide a real-time stress assessment system in accordance with various embodiments.

The device 100 comprises a hand-held device, such as a smartphone, that includes a display screen and various device features. The device 100 includes an application 102 that is executed by a processor of the device to perform various stress management functions. The device 100 also includes a camera 104 to capture still images and/or video images used for stress analysis. Additional hardware and software is provided to allow the device to communicate over a wireless interface 106. It should be noted that embodiments of the system are not limited for use with only device 100, but can be used with any type of alternative devices 108 that can execute the application 102.

Figure 2:
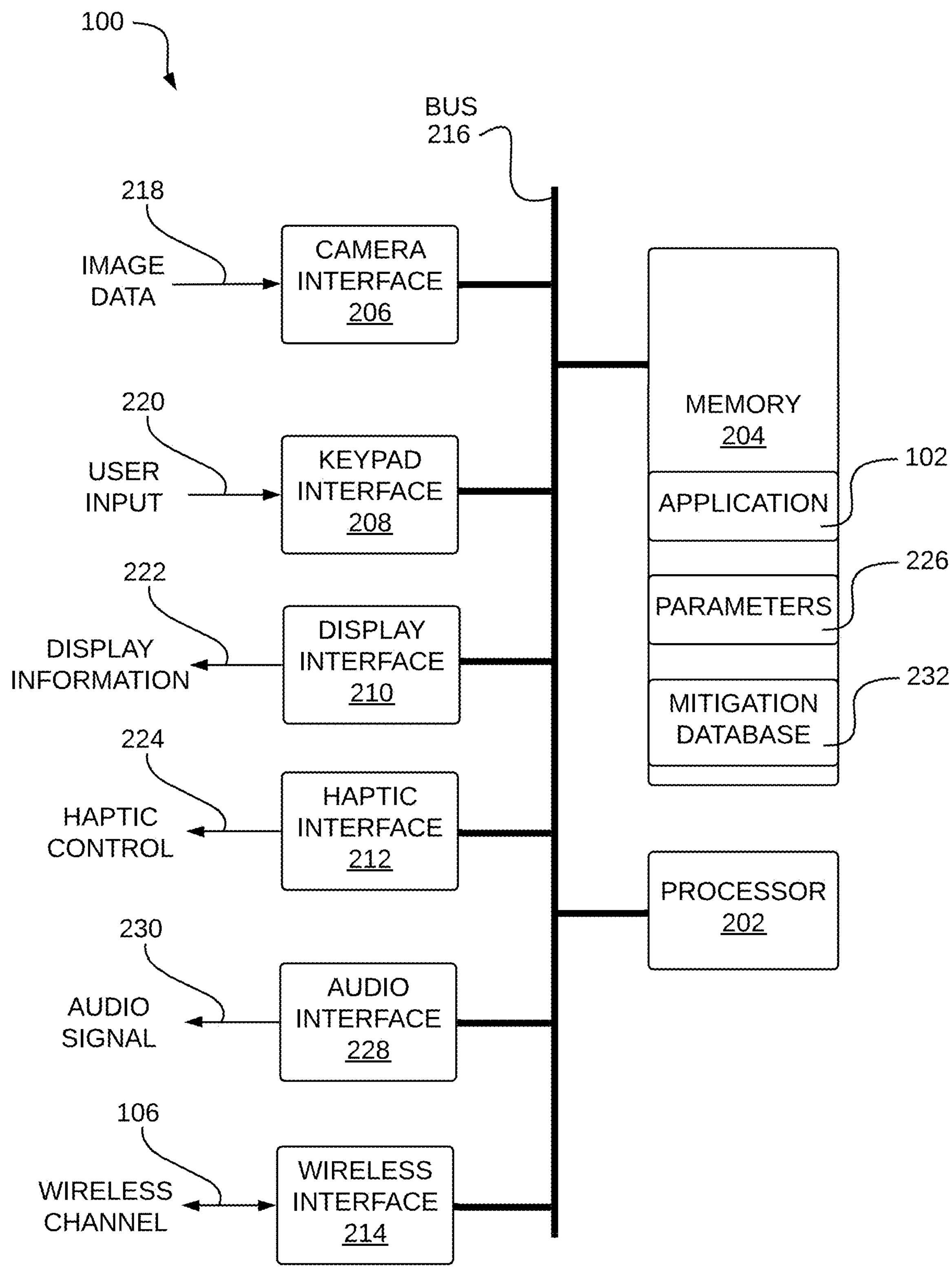
FIG. 2 shows a detailed exemplary embodiment of the device shown in FIG. 1.

FIG. 2 shows a detailed exemplary embodiment of the device 100 shown in FIG. 1. In one embodiment, the device 100 comprises a processor 202, memory 204, camera interface 206, keypad interface 208, display interface 210, haptic interface 212, audio interface 228, and wireless interface 214, all coupled to communicate over bus 216.

In one embodiment, the memory 204 stores the application 102 that comprises instructions which are retrieved and executed by the processor 202 to perform the operations of the stress assessment system. The memory 204 also stores parameters 226, such as blood flow parameters, that are generated and used by the application 102 during execution. The memory 204 also stores a mitigation database that maintains mitigation strategies to be presented to a user based on a determined stress score. The user can also rate the mitigation strategies based on their effectiveness for the user to form a mitigation history or a user profile for a user that identifies mitigation strategies utilized by the user and their associated effectiveness rating.

In one embodiment, the device 100 executes the application 102 and determines a physical stress level of a user. In an aspect, the camera interface 206 operates to receive image data 216 (still images and/or video) from a device camera and passes this image data to the memory 204 for storage and/or the processor 202 for processing.

In one embodiment, the keypad interface 208 operates to receive user input 218 from a keypad and passes this user input 218 to the memory 204 for storage and/or the processor 202 for processing.

In one embodiment, the display interface 210 operates to receive display information 222 from the processor 202 and passes the display information 222 to a device display, such as an LCD display located on the device 100.

In one embodiment, the haptic interface 212 operates to receive haptic control commands 224 from the processor 202 and passes the haptic control commands 224 to one or more haptic devices, such as a vibration device located on the device 100.

In one embodiment, the audio interface 228 operates to receive an audio signal 230 from the processor 202 and passes the audio signal 230 to one or more sound reproducing devices, such as an audio speaker located on the device 100.

In one embodiment, the wireless interface 214 operates to transmit and receive wireless data over a wireless channel 106 to/from another entity, such as a system communicating over the Internet.

Description of Operation

In various exemplary embodiments, the device 100 performs as a portable stress-assessment device according to the invention and is configured to obtain a plurality of digital electronic images of at least one region of interest (ROI) of a user's skin, preferably from the face of the user being evaluated for acute psychological stress. For example, the images are obtained by camera interface 206 from the camera 104 and passed to the processor 202 for processing.

The processor 202 executes the application 102 and operates to decompose some or all of the plurality of digital electronic images of the region(s) of interest into a plurality of color channels each corresponding to a different color. In some preferred embodiments, motion in the image data from at least the plurality of digital electronic images to be analyzed is compensated for.

In some preferred embodiments, the processor 202 is additionally configured to perform at least one processing operation (e.g., resampling, band filtering, thresholding, etc.) on some or all of the signals from the plurality of color channels to obtain one or more processed color channel signals. Peaks are preferably detected in at least one, some, or all of the processed color channel signals. Such peaks preferably correspond to heartbeats (or other defining characteristics (or proxies therefor) of heartbeats, or intervals (or proxies therefor) between heartbeats) used to define a blood flow parameter associated or correlated with psychological stress, examples of which include heart rate variability (HRV) and/or heart rate (HR).

The processor 202 is further configured to compute a value or statistics for the defining characteristic(s) of heartbeats (or proxies therefor) for the blood flow parameter(s) being assessed (e.g., heart rate variability (HRV) and/or heart rate (HR)) in the processed color channel signal(s).

The processor 202 is further configured to perform at least one of the following on the resulting values or statistics: storage (locally in memory 204 or on an operably associated storage device); transmission over a network using the wireless channel 106 operably associated with the device; and outputting to the user a result reflecting the result of the stress assessment. For example, the result can be output to a haptic device using the haptic interface 212 or a audio device using the audio interface 228

The application 102 provides blood-flow based stress assessment functionality and resides in whole or in part on the device 100 itself and/or in the cloud (i.e., a computing model where services are delivered and used over the Internet (via wireless channel 106) on an as-needed basis, relying on shared computing resources rather than local servers or personal computing devices to run applications. In some embodiments, when such a device (or cloud-based system in communication with the device 100) determines that a user is experiencing psychological stress, the device communicates that determination to the user. That determination can also be transmitted to one or more third parties (e.g., the user's doctor or psychologist, a family member, etc.) or other resources (e.g., a cloud-based electronic medical record, a cloud-based data repository that stores data for subsequent analysis, etc.).

In one embodiment, the camera 104 of the device 100 is a forward-facing camera and is used to acquire electronic image data 218 from one or more regions of interest (ROI) on the skin of the user. Preferably, the regions of interest imaged by the camera are highly perfused with blood to facilitate analysis of one or more blood flow parameters correlated or associated with psychological stress, for example, heart rate (HR) and/or heart rate variability (HRV). In various embodiments, preferred regions of interest of human skin include areas of the face, hands, arms, and neck, as they are not only highly vascularized and perfused but are also easily imaged by the user using the camera of her/his smartphone or other camera-bearing personal portable handheld computing device.

Image data 218 collected from the subject's skin is analyzed by the processor 202 to determine if the blood flow parameter(s) being used for the assessment indicate that the subject is then experiencing psychological stress. If so, or if not, depending on the configuration of the device (and/or its associated cloud-based system), the processor 202 may inform the subject of the result via an output, for example, a visual, auditory, or other haptic signal.

Furthermore, if the subject is determined to be experiencing stress, in one embodiment, the processor 202 (and/or system) is configured to provide the subject with one or more interventions (or stress mitigation strategies) designed to reduce or alleviate the subject's stress. Examples of such interventions include, but are not limited to, providing videos, podcasts, or the like to the subject through the device 100 to facilitate meditation, relaxation, or the like, as well as suggestions to contact or visit a counselor, etc. Other examples of interventions that can be provided in accordance with the embodiments include having a counselor or other medical professional call or otherwise communicate with the subject in the event s/he is determined to be experiencing psychological stress. As described in greater detail below, a user can rate the effectiveness of the mitigation strategies and the processor 202 can utilize these ratings to filter potential mitigation strategies to generate mitigation strategies presented to the user in response to subsequent stress events.

Certain particularly preferred embodiments of the stress assessment system are implemented on smartphones configured to function on-demand as handheld, real-time stress assessment devices. In many such embodiments, the stress assessment application 102 running on the smartphone compares calculated values for the measured blood flow parameters to a historic normal (i.e., when the subject is in a relaxed, non-psychologically stressed state) value of those parameters for the subject. For the particular parameter being measured, the application 102 determines if the measured current value is greater or less than the historic value for that parameter when the subject is not experiencing psychological stress. Alternatively, or in addition, the application 102 (or cloud-based system) may also determine if the difference between the currently measured and the historic normal value for that parameter exceeds (or falls below, as the case may be for the particular parameter) a predetermined threshold. If so, the application 102 may direct the device to signal to the subject that s/he is then psychologically stressed. If not, the application 102 directs the device to either output no signal (which the subject would then take to mean that no stress was detected by the particular assessment) or to output a signal (e.g., an audio, haptic, or visual signal) to the subject (and/or one or more third parties) that no stress was detected.

Another aspect of the embodiments provides methods of assessing, preferably in real time, whether a subject is experiencing psychological stress through the use of a portable wireless stress-assessment device of the invention (e.g., a smartphone) to determine if one or more blood flow parameters correlated or associated with psychological stress are indicative of a state of psychological stress and, if so, generating an output corresponding to such assessment, preferably an output or signal that is discernible by the subject.

In preferred embodiments, the result of any such assessment, and preferably the associated data, is stored locally (as parameters 226) or in the cloud. If desired, such results can be communicated to a third party, for example, the subject's healthcare provider. Such results can also be used to drive or otherwise prompt one or more automated communications (e.g., medication, mindfulness, or relaxation prompts, videos, podcasts, etc.) from, for example, a cloud-based health monitoring service, to the subject to relieve or reduce psychological stress if a particular assessment indicates that the subject was then determined to be experiencing such stress. Conversely, if an assessment indicates that a subject is not experiencing stress, those results could be used to drive or otherwise prompt one or more automated communications aimed to help the subject maintain a non-stressed state (e.g., a text message with positive reinforcement).

In general, the value of a particular blood flow parameter associated or correlated with psychological stress is measured in real-time using the device's camera. When multiple blood flow parameters are being measured, they are preferably measured concurrently (or at least the image data from which the parameters are assessed are captured concurrently, and are preferably derived from the same images), although analysis of the data for each parameter may be performed separately, be it in parallel or serially. A particular blood flow parameter can be measured using any suitable metric. For instance, for heart rate, in some embodiments it is measured in beats per minute, using the maximum value for each beat (it being understood that any other value (or proxy), e.g., the lowest value between heartbeats, that is suitable for measuring heart rate may also be used). In the context of HRV (i.e., the amount of variation in the intervals between heartbeats within a specific period, e.g., 5-300 seconds), the maximum value (or any suitable proxy thereof, e.g., 90% of the maximum value) for each heartbeat is preferably used.

In one embodiment, proxies based on or derived from measurements can also be used. For example, a proxy equal to 90% of a particular peak can also be used. Similarly, averages based on measurements derived from, for example, multiple images captured in rapid succession (e.g., 2-5) images captured by a forward-facing camera with high resolution and frame rate (e.g., 1920×1080 resolution and having a frame rate of 120 frames per second (fps)) may be used. In certain preferred embodiments, the application determines a value for the particular blood flow parameter being assessed from data extracted from each frame of image data captured by the device's camera.

Even though distance effects may occur in images captured by a camera of a device according to the invention, in one embodiment, those effects are computationally compensated to reduce their influence. Even so, it is preferred that a subject holds a device (i.e., a portable wireless device configured as such via software) at an appropriate distance to perform the desired blood flow parameter assessments.

Preferably, to conduct a psychological stress assessment, the distance from the camera to the skin region to be imaged should be about 5 cm to about 20 cm, with the subject trying to be as consistent as possible as to the camera-to-skin distance, and the skin region that is imaged for any given assessment and for multiple assessments over time.

In the context of the embodiments, image data can be collected in any desired way, although collecting high speed video (e.g., 30-120 fps or more) is preferred. The processor 202 is configured to analyze image data captured by the portable wireless device's camera using any suitable digital signal processing techniques or combinations thereof.

Heart rate variability is typically monitored noninvasively, frequently by electrocardiogramar by using a chest strap heart monitor. HRV measured using such conventional devices and approaches, as well as those according to embodiments of the invention, can be used to provide feedback about a subject's lifestyle, including the effectiveness of various interventions, such as the use of mindfulness and meditation techniques, different sleep strategies, exercise, etc. HRV monitoring is preferably performed periodically, at random or per a schedule. For example, one can monitor HRV one or more times daily or less frequently, for example, every other day, weekly, monthly, or some other interval. HRV monitoring can be performed at the same(s) or different time(s) of day as well. In some preferred embodiments, one monitors HRV on a daily basis, at or about the same time each day (e.g., at 7:30 am, after breakfast but before leaving for work, etc.).

As described, blood flow parameters associated or correlated with psychological stress include heart rate variability (HRV) and heart rate (HR), among others. With regard to HRV, if a person's system is in more of a fight-or-flight mode, the variation between heartbeats is lower (i.e., the person experiences acute psychological stress) as compared to when the person is in a normal, relaxed, unstressed state. With regard to HR, periods of acute psychological stress lead to increased HR as compared to an unstressed state.

Figure 3:
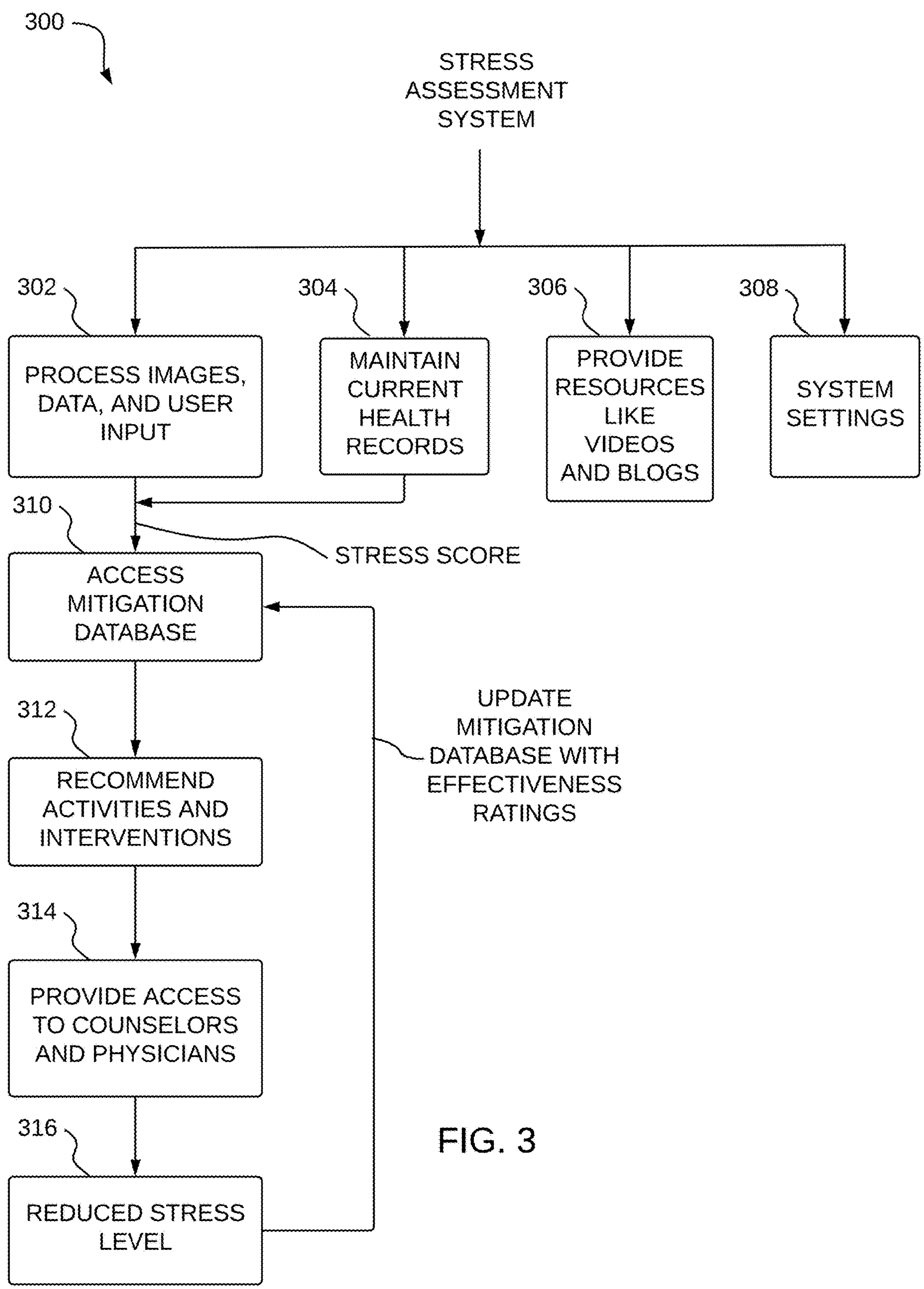
FIG. 3 shows an exemplary functional diagram of a stress assessment system.

FIG. 3 shows an exemplary functional diagram of a stress assessment system 300. The assessment system 300 performs a variety of functions at each functional block (FB) shown in FIG. 3.

At FB 302 the system processes images, data, and user input to generate information used to determine a stress score. For example, the images are captured by a portable device, such as the subject's mobile phone. The data is provided by health records from FB 304, which maintain a variety of health information about the subject.

The user input is provided by the subject in response to questions communicated to the subject through a device, such as the subject's mobile phone. All the information processed at FB 302 and FB 304 are used to generate a stress score for the subject.

At FB 310, the stress score is used to access a mitigation database to determine mitigation strategies, activities and/or interventions that a user can use to mitigate stress. The mitigation database is updated with user effectiveness ratings that indicate the types of mitigations that are useful and effective and those that are not useful and effective at mitigating stress. In response to future stressful events, the effectiveness ratings can be used to filter potential mitigation strategies to determine and present those strategies that are rated as effective for the user.

At FB 312, based on the stress score and the mitigation database, activities and interventions are recommended. For example, the subject may be advised to deep breath, meditate, listen to music or a podcast, or to speak with a counselor depending on the level of the stress score.

At FB 314, access to counselors and physicians is provided. Thus, a particular counselor or physician can be recommended to the subject based on the stress score.

At FB 316, the subject experiences reduced a stress level in response to performing the recommended interventions. The subject also provides ratings of the effectiveness of the mitigation strategies to the mitigation database to update the effectiveness of mitigations utilized by the user and how successful they have been at reducing stress. Thus, unsuccessful and/or ineffective mitigation strategies may not be recommended to the user more than once.

At FB 304, the system maintains health records for the subject. The health records are provided as part of the overall stress score.

At FB 306, resources for use by the subject are maintained or accessible. For example, the resources may include videos, music, or blogs that can be utilized by the subject to reduce stress levels.

At FB 308, system settings are provided that identify connected devices, provide security, user profiles, and provide payment processing functions.

Therefore, the stress assessment system 300 operates to determine in real-time a person's stress level, and if the stress level is higher than a threshold level, provide mitigation strategies, recommendations, and interventions to the user that can be used to reduce the stress level. The successfulness and/or effectiveness of recommended mitigations are tracked and a mitigation database is maintained so that ineffective mitigations are not recommended to the user.

Figure 4A:
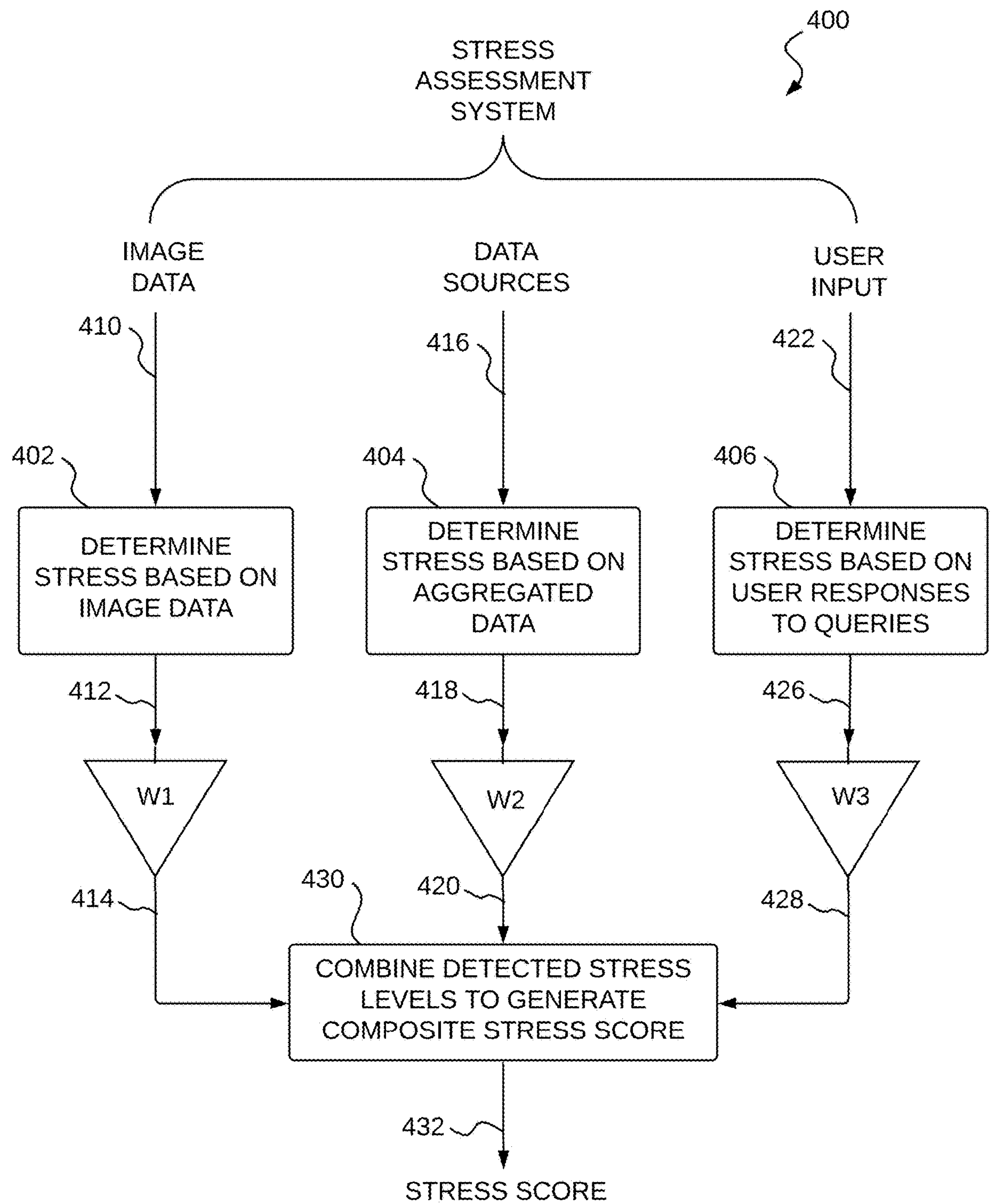
FIG. 4A shows a diagram that illustrates the operation of an exemplary embodiment of a stress assessment system in accordance with the invention.

FIG. 4A shows a diagram that illustrates the operation of an exemplary embodiment of a stress assessment system 400 in accordance with the invention. The assessment system 400 comprises processing blocks (PB) 402, 404, and 406, weights W1-3, and combiner 430. In various embodiments, the operations at each processing block are performed by the processor 202 executing the application 102 in the memory 204 and in conjunction with other functional blocks at the device 100.

During operation, the PB 402 receives image data 410 from a camera on a portable device, such as the device 100. The image data can be still images or video images of a ROI of a subject or device user. The PB 402 processes the image data to determine a cognitive stress value 412 that indicates the stress experienced by the subject based on the processing of the image. For example, the cognitive stress value 412 reflects various stress experienced by the subject based on health, financial status, family issues, and/or other stressful situations experienced by the subject. The cognitive stress value 412 is adjusted by the weight W1 to generate a weighted cognitive stress score 414 (e.g., in the range of 0-5) that is input to the accumulator 430.

The PB 404 receives information 416 from various data sources, such as from medical records, sleep records, marriage status information, and/or job status information. The PB 404 processes the information 416 to determine a self-awareness stress value 418 that indicates the stress experienced by the subject based on various health and personal situations of the subject. The self-awareness stress value 418 is adjusted by the weight W2 to generate a weighted self-awareness stress score 420 (e.g., in the range of 0-5) that is input to the accumulator 430.

The PB 406 receives user input 422 from the subject in response to a variety of stress related questions. For example, the questions relate to sleep, pain, loneliness, and/or anxiety expressed by the subject in response to the questions. The PB 406 processes the user input 422 to determine a psychodynamic stress value 426 that indicates a stress level expressed by the user in response to the questions. The psychodynamic stress value 426 is adjusted by the weight W3 to generate a weighted psychodynamic stress score 428 (e.g., in the range of 0-5) that is input to the accumulator 430.

Figure 4B:
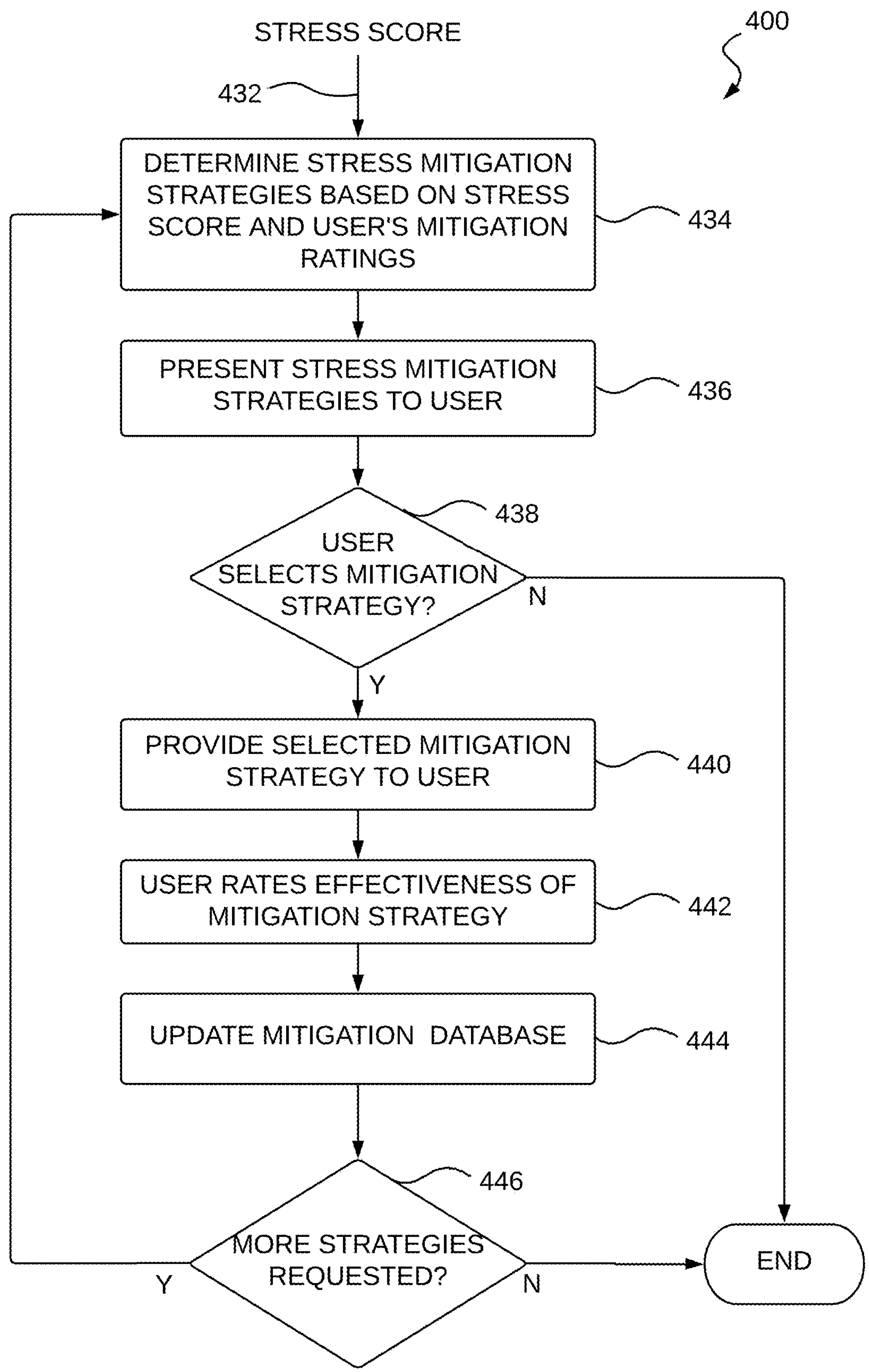
FIG. 4B shows a continuation of the diagram shown in FIG. 4A that illustrates the operation of an exemplary embodiment of a stress assessment system 00 in accordance with the invention.

The combiner 430 receives and combines the weighted scores 414, 420, and 428 to generate a composite stress score 432 that is output to the PB 434 shown in FIG. 4B. Any suitable combining method or algorithm can be used to combine the weighted scores 414, 420, and 428 to generate the composite stress score 432.

FIG. 4B shows a continuation of the diagram that illustrates the operation of an exemplary embodiment of a stress assessment system 400 in accordance with the invention.

The PB 434 receives the composite stress score 432 and uses this score to determine one or more mitigation strategies that can be used by the subject to mitigate the stress the subject is experiencing. In an embodiment, the processor 202 accesses the mitigation database 232 using the determined stress score to determine the mitigation strategies to recommend to the user. The processor 202 may also filter the mitigation strategies by their effectiveness ratings so that strategies that have already been rated as ineffective by the user are not presented again to the user.

At block 436, the determined mitigation strategies are presented to the user. For example, processor 202 presents the determined mitigation strategies to the user using one or more of the display interface 210, haptic interface 212, audio interface 228, and/or wireless interface 214.

At block 438, the user selects one or more mitigation strategies to perform for stress relief. For example, the user may select to perform a breathing exercise and/or listen to relaxing music. In one embodiment, the user indicates the selected strategies by providing user input using the keypad interface 208.

At block 440, the selected mitigation strategy is provided to the user. For example, the processor 202 the display interface 210, haptic interface 212, audio interface 228, and/or wireless interface 214 to provide the selected mitigation strategy to the user. For example, the processor 202 may access relaxing music using the wireless interface 214 and play this music using the audio interface 228.

At block 442, the user rates the effectiveness of the selected mitigation strategy. For example, the user rates how effective listening to music is to reduce the user's stress level. In one embodiment, the user provides the rating as user input using the keypad interface 208.

At block 444, the user rating is used to update the mitigation database. For example, the processor 202 receives the user rating of the selected mitigation strategy and updates the mitigation database to include the rating provided by the user. Thus, the mitigation database includes effectiveness ratings for mitigation strategies utilized by the user. Those strategies that are rated as ineffective may not be presented to the user in the future.

At block 446, a determination is made as to whether more mitigation strategies are requested by the user. For example, the user may perform a first mitigation strategy and then request a second mitigation strategy. If no additional mitigation strategies are requested, the method ends. If additional mitigation strategies are requested, the method proceeds to block 434. It should be noted that the rating provided at block 442 and stored in the database at block 444 are used at block 434 to determine additional stress mitigation strategies for the user.

Thus, method 400 operates on a portable device, such as device 100, to provide stress detection and stress mitigation to a device user. It should be noted that the operations of method 400 are not limiting and that the operations can be rearranged, added to, deleted, changed or otherwise modified within the scope of the stress management system.

Figure 4C:
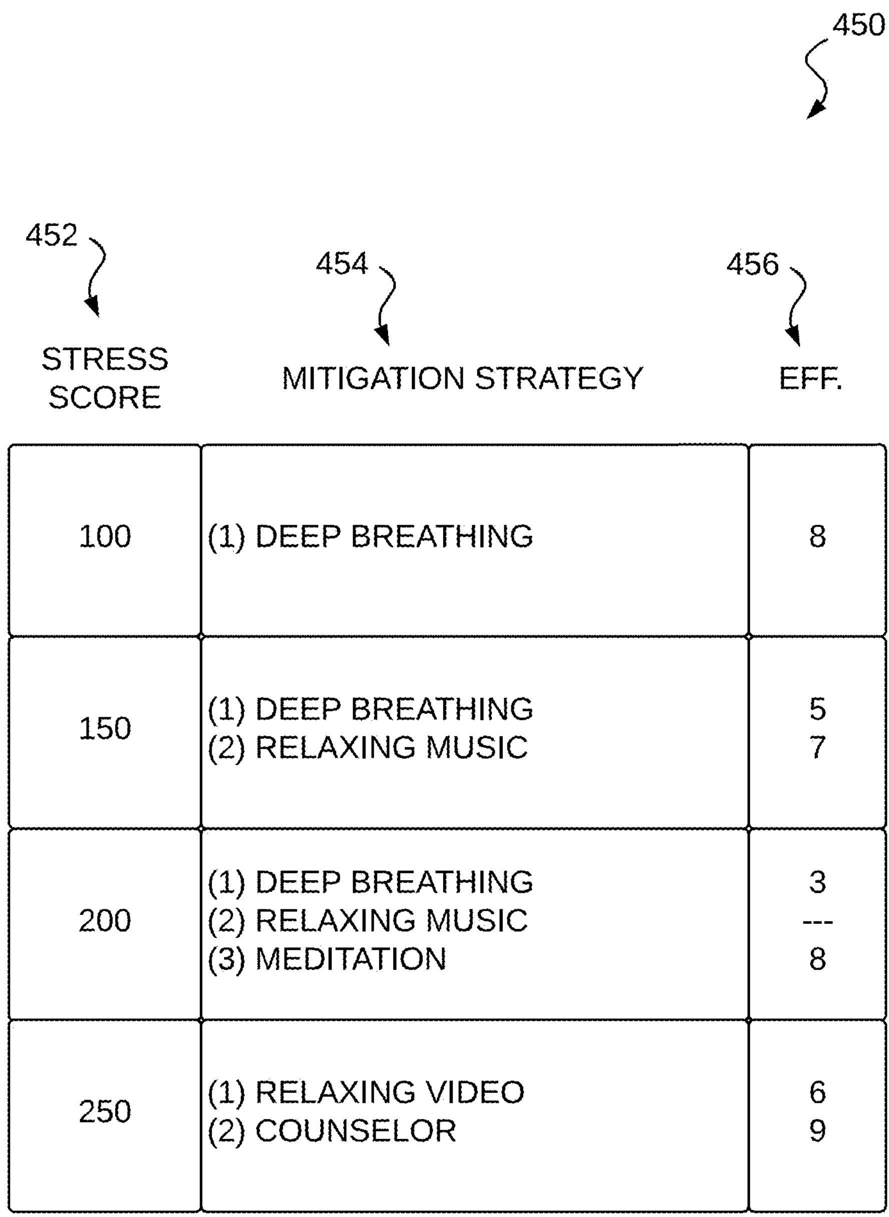
FIG. 4C shows an exemplary embodiment of a mitigation database.
Figure 29:
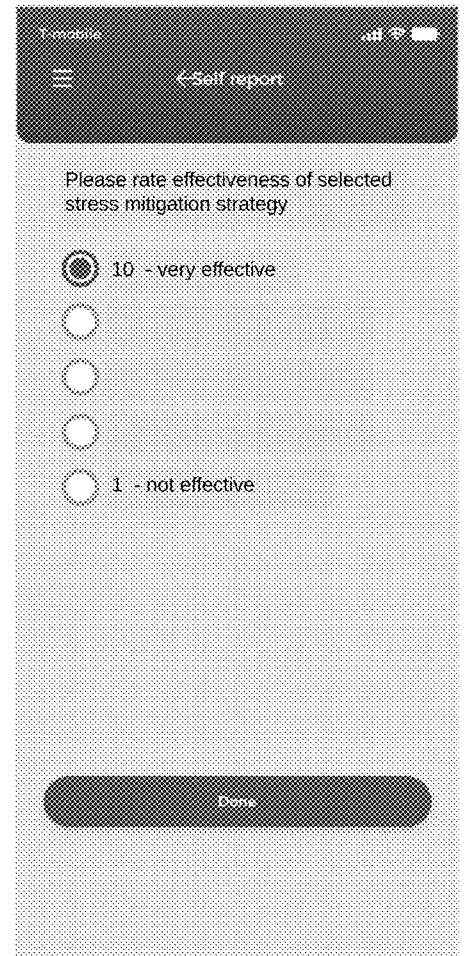

FIG. 4C shows an exemplary embodiment of a mitigation database 450. For example, the database 450 is suitable for use as the mitigation database 232 shown in FIG. 2. The mitigation database 450 comprises a plurality of stress scores 452 that are each associated with one or more mitigation strategies 454. Each mitigation strategy 454 has a user effectiveness rating 456 that indicates how effective that strategy was in relieving stress for the user when the user was experiencing stress that resulted in the associated stress score. In one embodiment, the effectiveness ratings 456 are provided on a scale of 1 to 10 with 10 being "very effective" and 1 being "not effective." In an embodiment, the user provides the effectiveness rating 456 to the processor 202 as user input using the keypad interface 208 in response to the screen display as shown in FIG. 29. The processor 202 updates the mitigation database 450 with the received user ratings.

Figure 5:
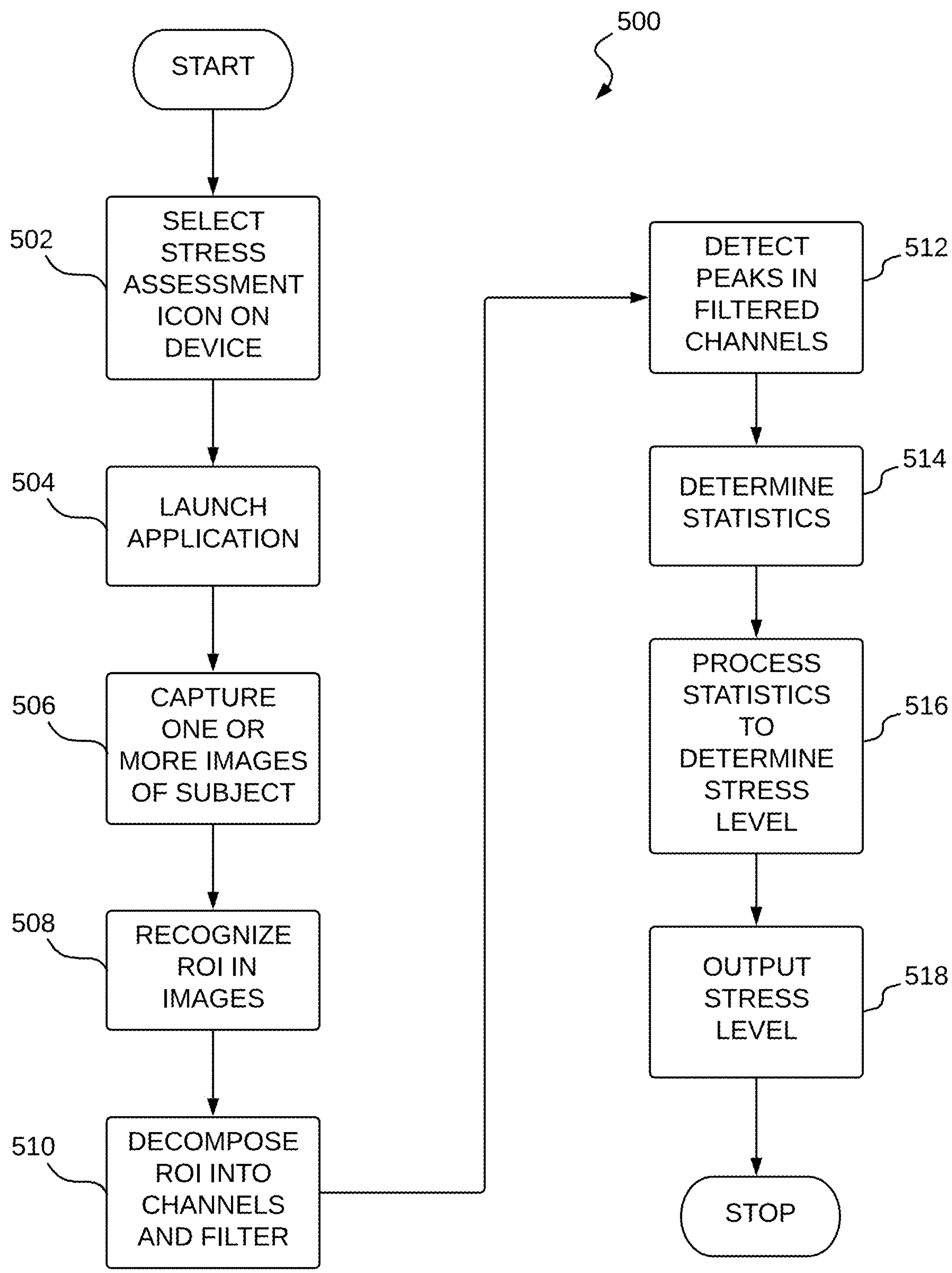
FIG. 5 shows an exemplary embodiment of a method 500 for measuring a person's stress in real-time.

FIG. 5 shows an exemplary embodiment of a method 500 for measuring a person's stress in real-time. For example, method 500 is performed by the device 100, which operates to analyze digital images of a region of interest of a subject's skin that has internal blood flow sufficiently near the surface to allow analysis of one or more blood flow parameters. Preferably, images of the skin of the subject's face (or one or more regions thereof) is used and that data is processed by the processor 202 to calculate whether the subject is experiencing acute psychological stress. In one embodiment, the method 500 is suitable for use at block 402 shown in FIG. 4A to determine user stress based on image data.

The method 500 begins at block 502 by configuring the device 100 to perform a stress assessment, which can occur when a user wishes to assess her/his stress level. For example, the user selects a stress assessment icon on her/his smartphone to launch the stress assessment application 102 according to the invention.

At block 504, the application 102 is launched and directs the user to use the smartphone's camera to collect image data of a desired, preferably pre-selected, portion of her/his body, for example, her/his face. Among the instructions provided are those regarding how the subject should behave while the device's camera captures images of the portion of the user's body. For example, the instructions may direct the user to not move or identify the preferred distance between the camera and body part being imaged. Instructions can be provided to the user via the device's output display (e.g., a touchscreen in the case of a smartphone). Alternatively, some or all of the instructions can be auditorily output from the device 100 (e.g., through an onboard speaker or a bluetooth-connected pair of speakers). In one embodiment, the application 102 directs the device 100 to display to the user a video clip containing the instructions. Exemplary instructions may include such elements as instructing the user to sit or stand in a comfortable position in front of the device with the camera pointed toward the region of interest (ROI) to be imaged (e.g., the person's face). Other instructions instruct the user to place the device about 18-20 inches from the ROI in a stable position so that the ROI is within the field of view of the device's camera. Other instructions turn the device's camera on and allow it to focus on the body part to be imaged and record video (preferably at a preset resolution, frame rate, etc.) while the user minimizes movement during the image capture phase (e.g., 10-300 seconds). In some embodiments, the application's instructions may ask the user to smile or talk about her/his daily activity for a short period of time (e.g., 10-20 seconds) in front of the camera.

In some embodiments, before capturing image data, the application 102 may ask the user one or more pre-selected questions, and the answers to the questions are recorded. The questions may be selected to capture variations in emotional states, sleep quality, mood, physical activity, perception of the person's own health state, whether medications have been ingested, etc. If responses are verbally recorded using a microphone of the device, aspects of the user's response, such as tonal variations, pace or cadence of speech, etc. may also be analyzed.

At block 506, the device 100 captures one or a plurality of digital images using its camera. For example, the device 100 may take a video of the person's face during the video capture phase of the process. Image capture may be performed in response to a subject activating the camera, e.g., via a voice or touch command, to begin video recording, or automatically, for example, after a predetermined period after the instructions are displayed, an acknowledgment is provided, or the like.

In some embodiments, the portion of the subject being imaged, e.g., her/his face, is automatically detected in the captured video using any suitable detection algorithm adapted to detect that body part (or portion thereof). Preferably, images are automatically stabilized or otherwise motion compensated to produce accurate images.

At block 508, one or more specific regions of interest (ROI) of the imaged body part are recognized in the captured and compensated video. For example, when a subject's face is the body part that is imaged, an automatic facial feature detection algorithm or module is activated by the application 102. Particularly preferred facial regions for detection and assessment of variation in blood flow parameters associated with psychological stress in accordance with the invention include the skin around the eyes, nose, and/or mouth (e.g., near the lips), as these ROI provide signals useful for assessing heartbeat-related parameters in color channels obtained from images of such regions, as discussed further below. In some embodiments, the application 102 provides a statistical clustering algorithm that is used to detect regions of interest in the captured images. Preferred regions of interest are those in sets of continuous pictures that provide a high degree of information about blood flow in the imaged region of skin.

In some embodiments, after the application 102 performs motion compensation (for example, using a standard local optic flow algorithm) and identification of one or more regions of interest, the application 102 filters the image data using a bandpass spatiotemporal filter (such as a spatiotemporal Gabor filter) with the temporal and spatial bandwidths set appropriately for the particular detection result. For each pixel and each color channel, the correlation with neighboring pixels and color channels can be computed. For instance, the application 102 computes this correlation by treating the temporal power spectrum of each pixel/color channel as a vector and then computes the inner product between this vector and the vectors of neighboring pixels. The application 102 can also use other algorithms that provide similar results (e.g., canonical correlation, cross power spectrum analysis, etc.). Preferably, for each pixel, the likelihood that the pixel is skin color is computed. This can be achieved, for example, using a standard probabilistic filter based on frequencies of color values of human skin. A standard computer vision object recognizer can be used for each pixel to provide the likelihood that the pixel corresponds to a part of the human body (e.g., using a face detector, hand detector, arm detector, etc.). The information from the correlation filter, the color skin filter, and the object recognition filters can then be combined using standard sensor fusion approaches (e.g., Bayesian inference, a neural network, etc.). A result of such routines may be an image with the probability for each pixel that the pixel provides relevant blood flow information.

At block 510, the application 102 operates to decompose the ROI data into a plurality of channels, each corresponding to a different color. For example, the channels can be green, red, and blue ("RGB") channels. Signals from one, some, and preferably all of the different color channels are then processed for further use, although in some preferred embodiments the channels are resampled to improve temporal resolution. For example, in some preferred embodiments such processing involves applying one or more spatial filters developed using canonical correlation analysis (i.e., analysis using cross-covariance matrices) or a similar supervised learning approach (such as a neural network or other suitable machine learning or artificial intelligence approach).

As will be understood, the objective of filtering is to predict the timing of the heartbeat-based parameters (or proxies of such parameters) derived from the captured, decomposed, and processed image data. Preferably, this part of the process focuses on analyzing data derived from the regions of interest, thus allowing the remaining portions of the image data outside of the ROI to be ignored. If desired, this approach can be applied to data from an individual pixel or to pluralities of adjoining or contiguous pixels. Indeed, filters can be used. The output of the spatial filters is then preferably passed through a temporal analysis algorithm or module to remove artifacts derived from earlier analyses of the particular blood flow parameter being assessed (e.g., human HRV).

Noise components from the signals can also be filtered out using, for example, a Kalman temporal smoother, to produce smoothed signals. If desired, bandpass or low- or high-pass filtering can also (or alternatively) be performed, depending on the particular blood flow parameter being assessed, the specific steps (e.g., algorithms, modules, routines, etc.) being used for processing signals, etc. Bandpass filtering may include, for example, a second order 1-3 Hz Butterworth bandpass filter. Thresholding may also be performed, wherein, for example, the channels are compared to a suitable fixed or variable threshold (e.g., some fraction the channel's standard deviation).

At block 512, the application 102 detects peaks (e.g., local maxima in the resulting channel signals) in the smoothed and processed signals. Such peaks may represent, for example, the peak value for each particular heartbeat in the data being analyzed, with the peak corresponding to, or acting as a proxy of or surrogate for "R" in a QRS complex, with the intervals between such peaks being used to determine heart rate variability, as the local maxima provide time estimates for heartbeat positions in the data. In preferred embodiments of HRV assessment, the time between peaks is used since it corresponds to the interval between consecutive heartbeats. If a plurality of different channels are processed, in some preferred embodiments the smoothed signals for one of the channels is selected for determining the intervals. For example, the smoothed signal for the channel having the most clearly defined peaks may be selected. Alternatively, a plurality or even all of the channels may be analyzed concurrently to determine each particular interval.

At block 514, the application 102 processes the time series of intervals between heartbeats obtained in the preceding step to derive one or more HRV values or statistics in the time domain, frequency domain, or in both domains. The application 102 performs the derivation of the HRV values or statistics from the data using any suitable method.

At block 516, the HRV statistics or values (or a subset thereof) are processed to assess whether the subject was experiencing acute psychological stress during the time the images were being captured. For example, the application 102 processes the statistics to determine the psychological stress experienced by the subject.

In one embodiment, any blood flow parameter associated or correlated with psychological stress at the time a stress assessment test is performed is compared to that parameter's value (or proxy) under steady-state, non-stressed, relaxed (i.e., reference) conditions. Such a comparison preferably involves comparing the parameter's value determined from image data captured at the time of stress assessment (i.e., "test conditions") with the value determined for the same parameter measured earlier when the subject was in a steady-state, non-stressed, relaxed condition (i.e., the "control" or "reference" conditions). In some embodiments, however, the reference (control) value for a particular parameter for a particular subject under a given set of conditions may be the result of reference testing of a population of other people, as opposed to subject her/himself.

It will also be appreciated that reference testing can be performed periodically, with the latest reference test results being used for subsequent stress assessments. This can be useful, for example, as a subject ages, changes medications and/or receives other forms of treatment, etc., or otherwise experiences health-related changes, family and/or relationship changes, education and/or professional changes, etc.

At block 518, the stress result is output. For example, the stress level is conveyed to the subject and/or other modules that are part of the application 102. For example, if the assessment determines that the subject was experiencing acute psychological stress during the time of the image capture phase, the result is conveyed to the subject as a visual and/or auditory result as well as being stored (locally the subject's device and/or remotely, for example, on a cloud-based server operably associated with the subject's device). That determination can also be communicated to one or more third parties (e.g., the subject's doctor or psychologist, a family member, etc.) or other resources (e.g., a cloud-based electronic medical record, a cloud-based data repository that stores data for subsequent analysis, etc.).

Thus, method 500 operates to measure a person's stress in real-time. It should be noted that the operations of method 500 are exemplary and can be rearranged, added to, deleted, changed, and/or otherwise modified within the scope of the embodiments.

In some embodiments, the subject's heart rate is assessed instead of, or in addition, to HRV in order to perform psychological stress assessment. As will be appreciated, the foregoing processes readily be adapted to utilize changes in heart rate, particularly an increase in heart rate as compared to the subject's heart rate when s/he is not experiencing acute psychological stress, to assess whether the subject experienced stress. The necessary adaptations to employ HR-based analytical framework and corresponding computational processes will be readily apparent to those in the art based on the foregoing description of a representative HRV-based process.

In one embodiment, the result of a stress assessment is combined with another indicator of acute psychological stress, such as an increased HR, increased BP, increased low frequency HRV, decreased high frequency HRV, a decreased galvanic skin response (GSR), increased baseline cortisol production, increased sympathetic activation, a decreased physiological response to acute stress, decreased baroreflex sensitivity, to confirm or strengthen a determination that a subject is experiencing acute psychological stress made using a portable wireless device according to the invention.

When a stress assessment reveals that a subject is experiencing psychological stress, the result can be output quantitatively, semi-quantitatively, or qualitatively to the subject, as well as to one or more other third parties, for example, a healthcare professional (doctor or psychologist), a family member, members of a support group, etc. A device or system of the invention may also inform the subject of the result via an output, for example, a visual, auditory, or other haptic signal, of a stress assessment.

FIGS. 6-31 are exemplary screenshots provided by one embodiment of a software application in accordance with embodiments of the invention. The software is operable on a computing device, such as a desktop computing device, a mobile device, or a headset.

Figure 6:
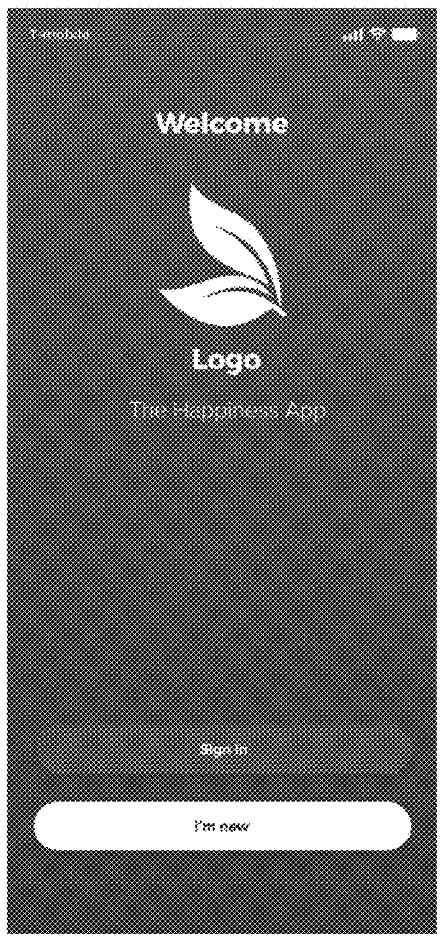
FIGS. 6-31 are exemplary screenshots provided by one embodiment of a software application in accordance with embodiment of the invention.

FIG. 6 is a screenshot of an initial graphical user interface (GUI) presented on a display by the software application.

Figure 7:
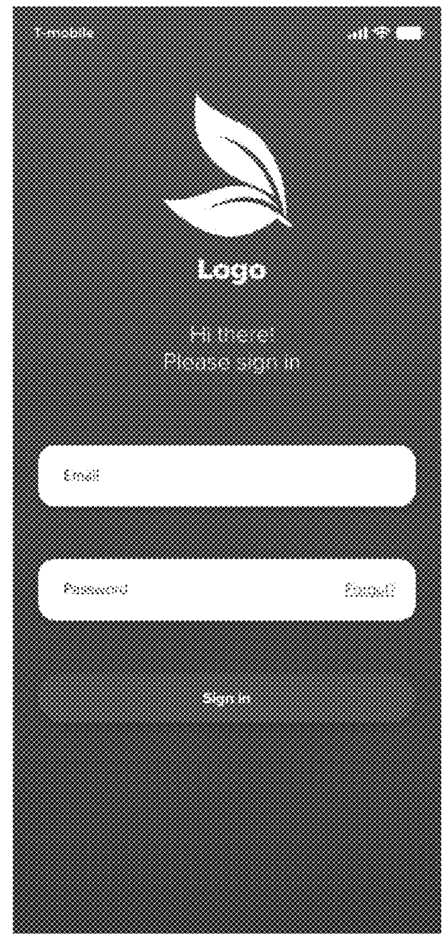

FIG. 7 is a screenshot of a login graphical user interface (GUI) presented on the display by the software application.

Figure 8:
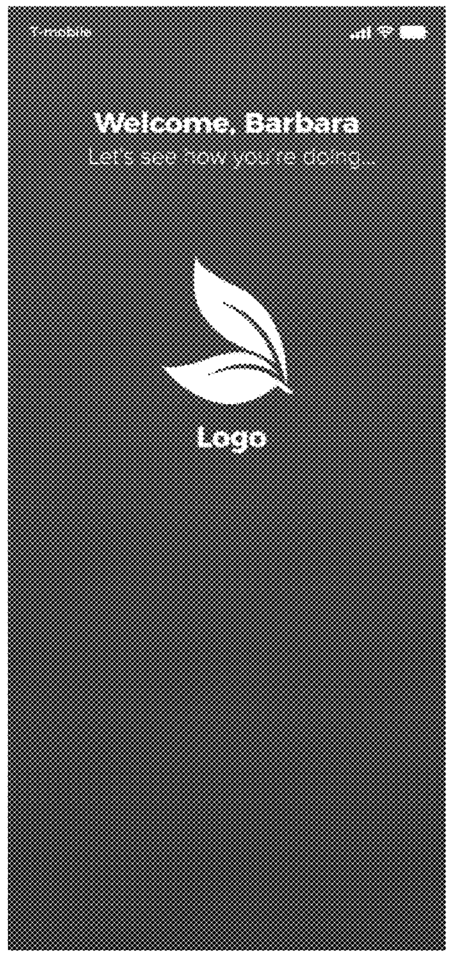

FIG. 8 is a screenshot of a welcome graphical user interface (GUI) presented on the display by the software application.

Figure 9:
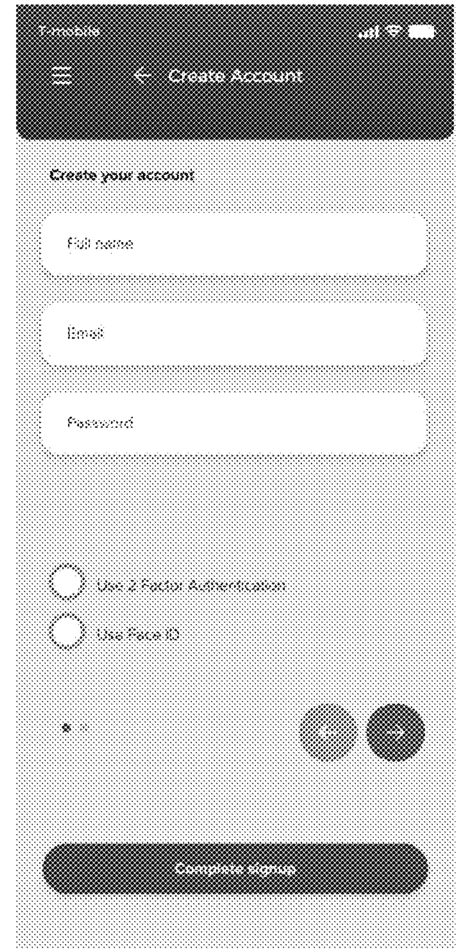

FIG. 9 is a screenshot of an account creation graphical user interface (GUI) interface presented on the display by the software application.

Figure 10:
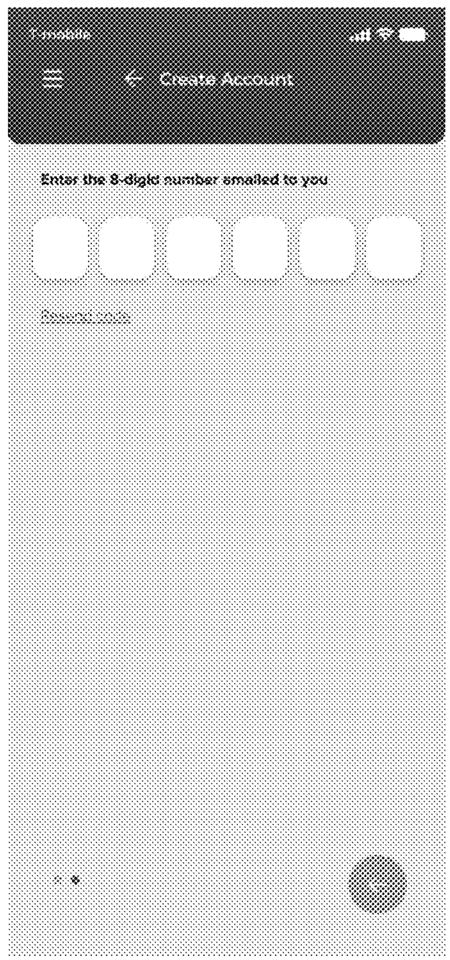

FIG. 10 is a screenshot of a two factor authentication challenge graphical user interface (GUI) interface presented on the display by the software application.

Figure 11:
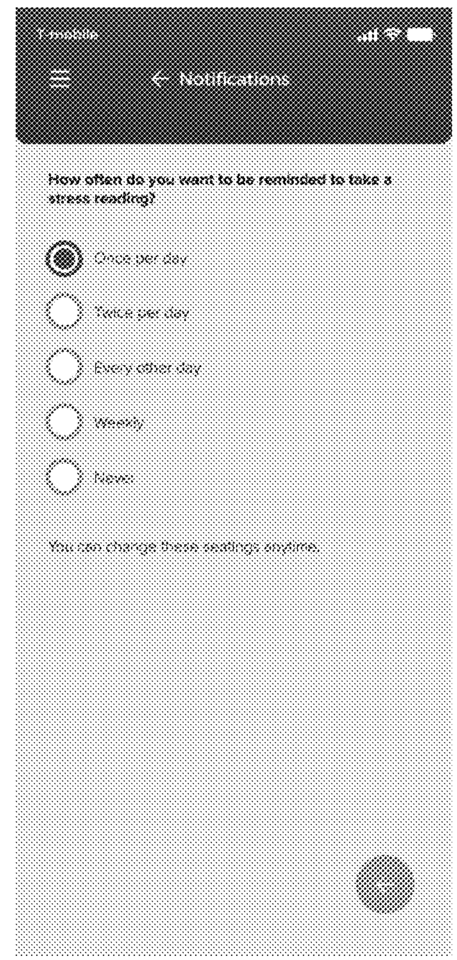

FIG. 11 is a screenshot of a stress reading configuration graphical user interface (GUI) interface presented on the display by the software application.

Figure 12:
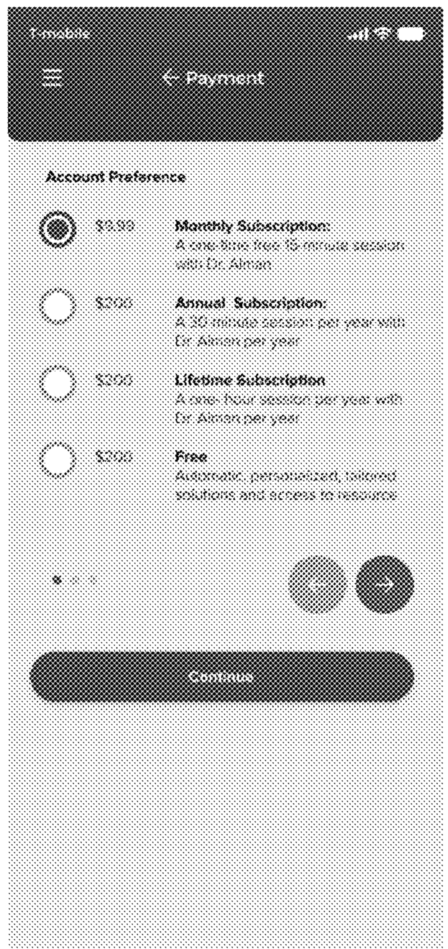

FIG. 12 is a screenshot of a pricing view and account selection graphical user interface (GUI) interface presented on the display by the software application.

Figure 13:
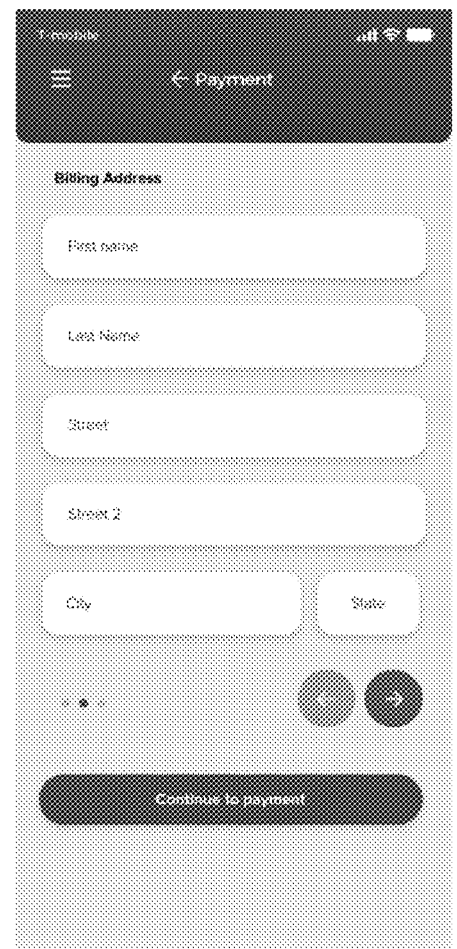

FIG. 13 is a screenshot of a billing address configuration graphical user interface (GUI) interface presented on the display by the software application.

Figure 14:
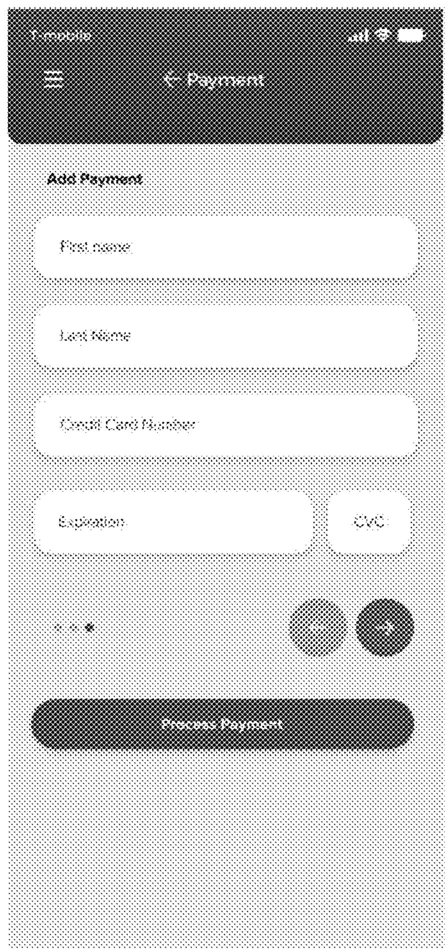

FIG. 14 is a screenshot of a payment prompt graphical user interface (GUI) interface presented on the display by the software application.

Figure 15:
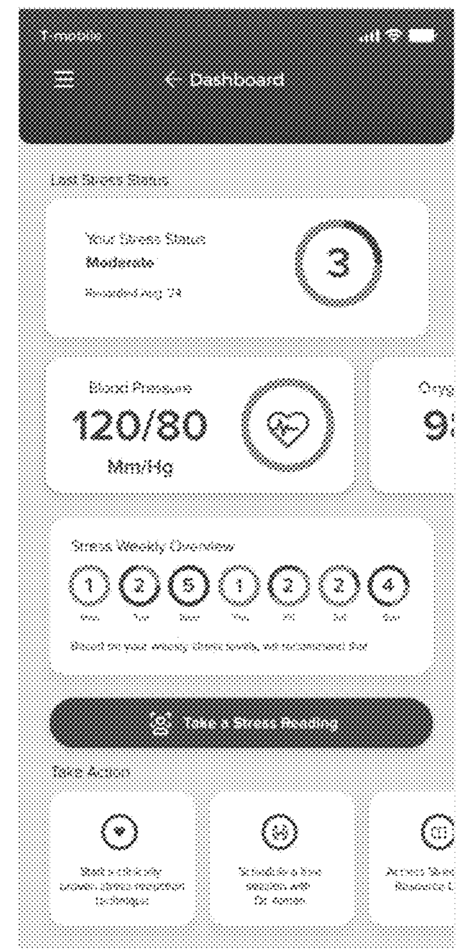

FIG. 15 is a screenshot of a dashboard graphical user interface (GUI) interface presented on the display by the software application.

Figures 16, 17:
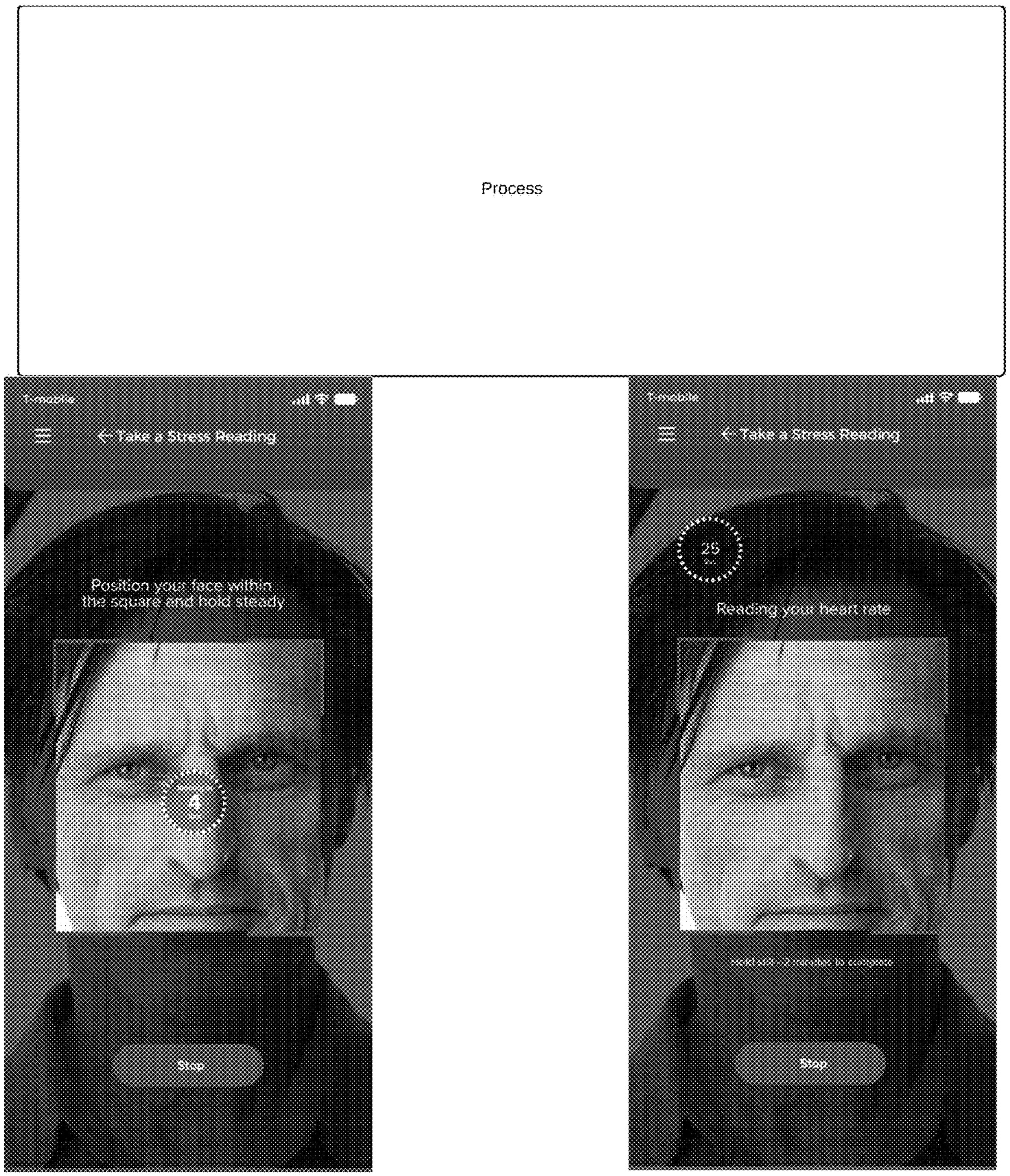

FIG. 16 is a screenshot of a stress reading graphical user interface (GUI) interface presented on the display by the software application.

FIG. 17 is a screenshot of the stress reading graphical user interface (GUI) interface during a heart rate reading performed by the software application using an image sensor.

Figure 18:
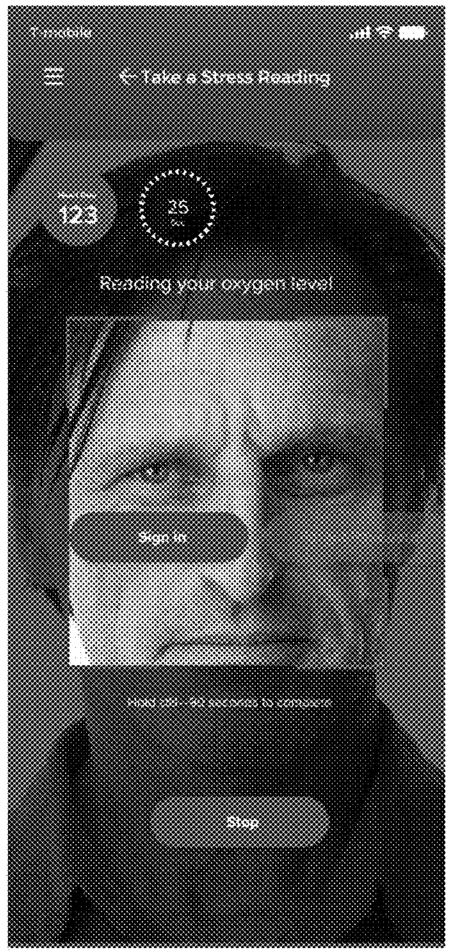

FIG. 18 is a screenshot of the stress reading graphical user interface (GUI) interface during an oxygen level reading performed by the software application using the image sensor.

Figure 19:
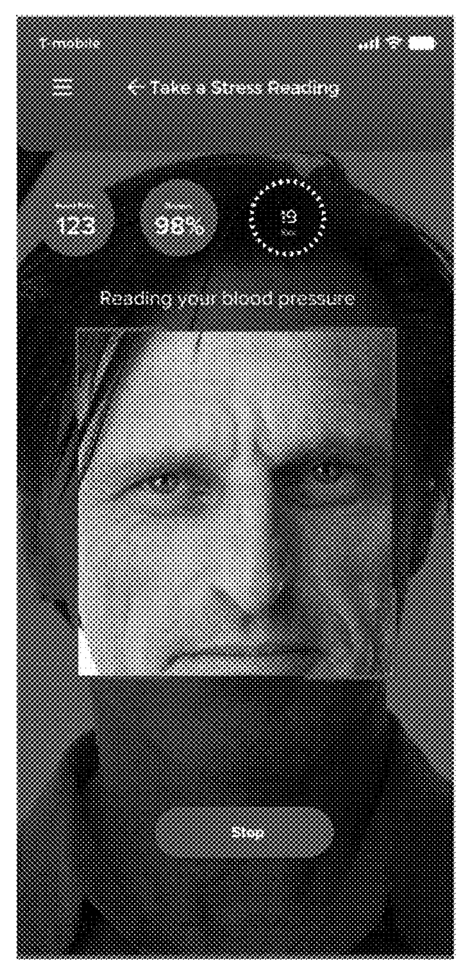

FIG. 19 is a screenshot of the stress reading graphical user interface (GUI) interface during a blood pressure reading performed by the software application using the image sensor.

Figure 20:
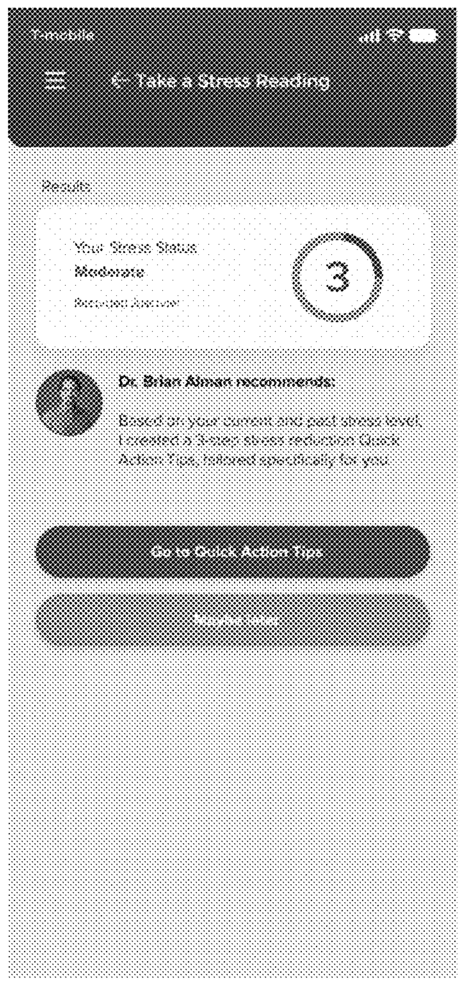

FIG. 20 is a screenshot of a stress result graphical user interface (GUI) interface provided by the software application. The stress result is provided after a stress reading is taken and provides stress status information and a link to quick action tips to mitigate any stress that is detected.

Figure 21:
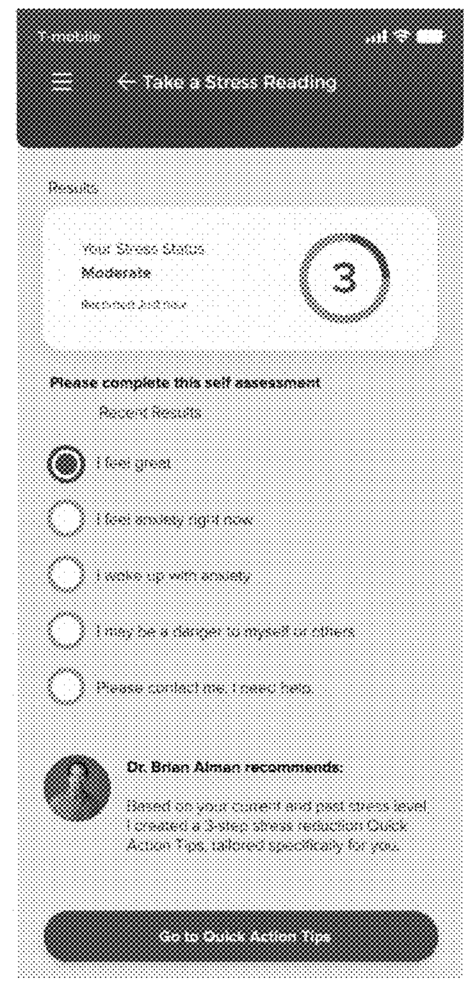

FIG. 21 is a screenshot of a stress result graphical user interface (GUI) interface provided by the software application. The stress result is provided after a stress reading is taken and provides a self assessment inquiry and a link to quick action tips to mitigate any stress that is detected.

Figure 22:
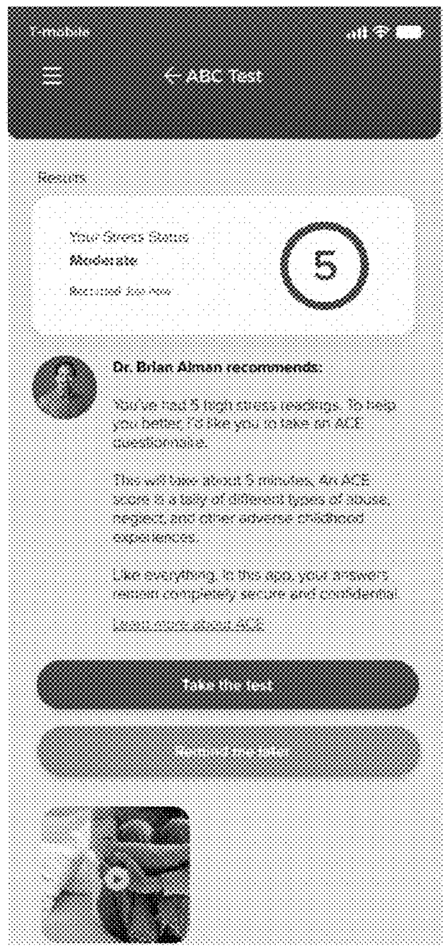

FIG. 22 is a screenshot of a stress inquiry graphical user interface (GUI) interface provided by the software application. The stress inquiry is provided after a selected number of high stress readings and offers the user an opportunity to take an ACE test to address any stress that is detected.

Figure 23:
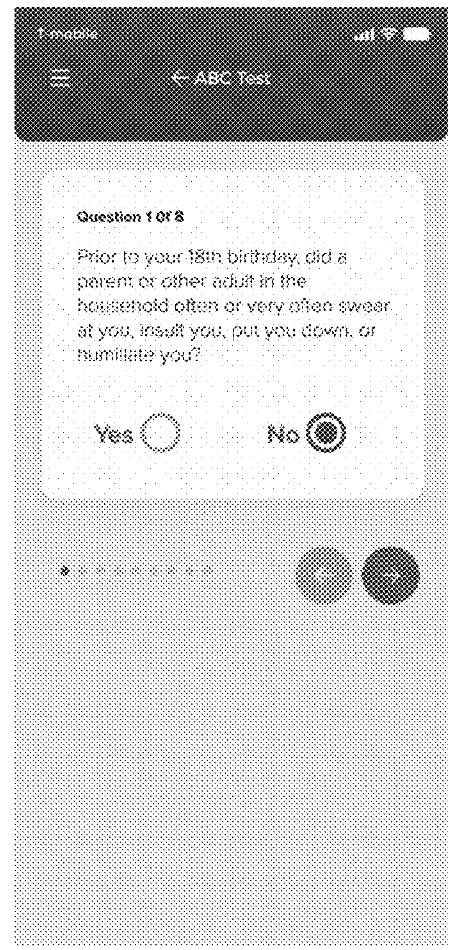

FIG. 23 is a screenshot of a graphical user interface (GUI) provided by the software application in which a first question of an 8-question ABC test is presented.

Figure 24:
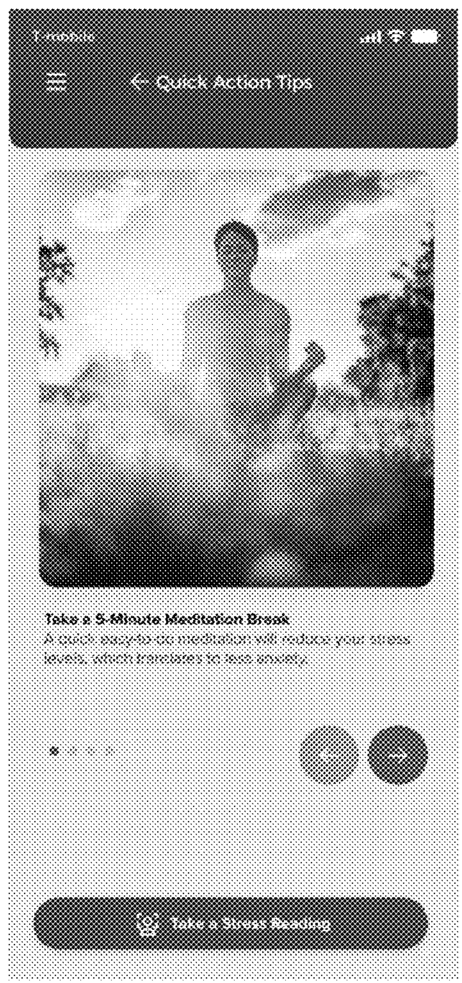

FIG. 24 is a screenshot of a graphical user interface (GUI) provided by the software application in which a quick action tip is presented.

Figure 25:
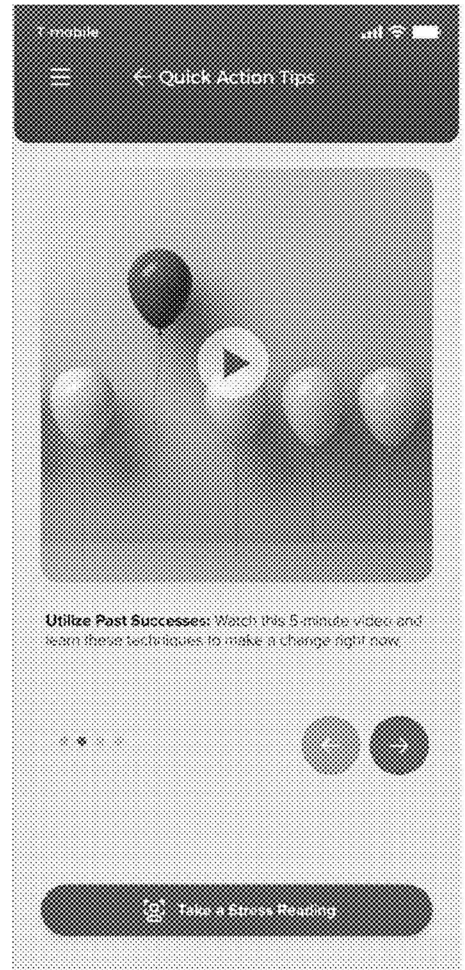

FIG. 25 is a screenshot of a graphical user interface (GUI) provided by the software application in which a "Utilize past success" video is presented.

Figures 26, 27:
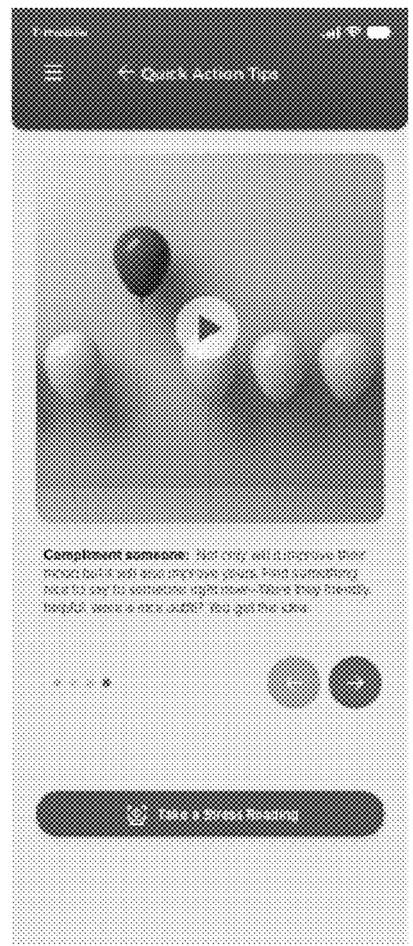

FIG. 26 is a screenshot of a graphical user interface (GUI) provided by the software application in which a "Break up the monotony" video is presented.

FIG. 27 is a screenshot of a graphical user interface (GUI) provided by the software application in which a "Compliment someone" video is presented.

Figure 28:
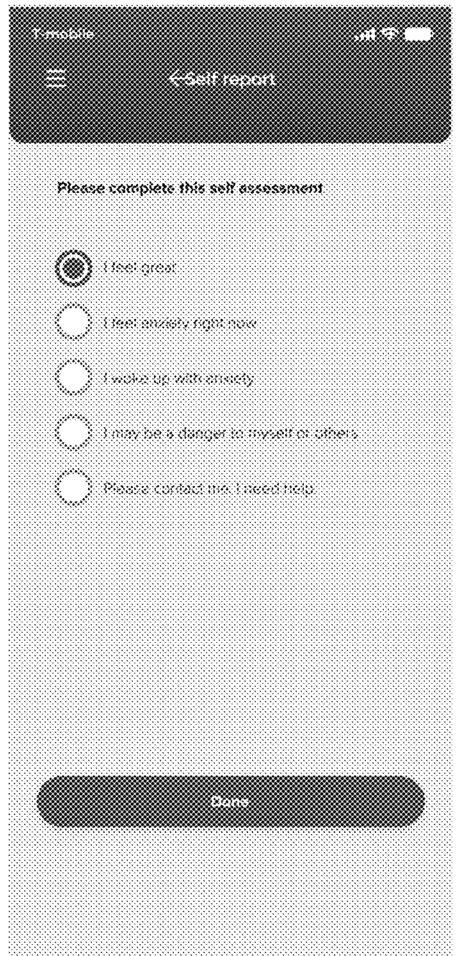

FIG. 28 is a screenshot of a graphical user interface (GUI) provided by the software application in which a self assessment inquiry is presented that is part of a self report.

FIG. 29 is a screenshot of a graphical user interface (GUI) provided by the software application in which a user rates the effectiveness of a selected stress mitigation strategy.

Figure 30:
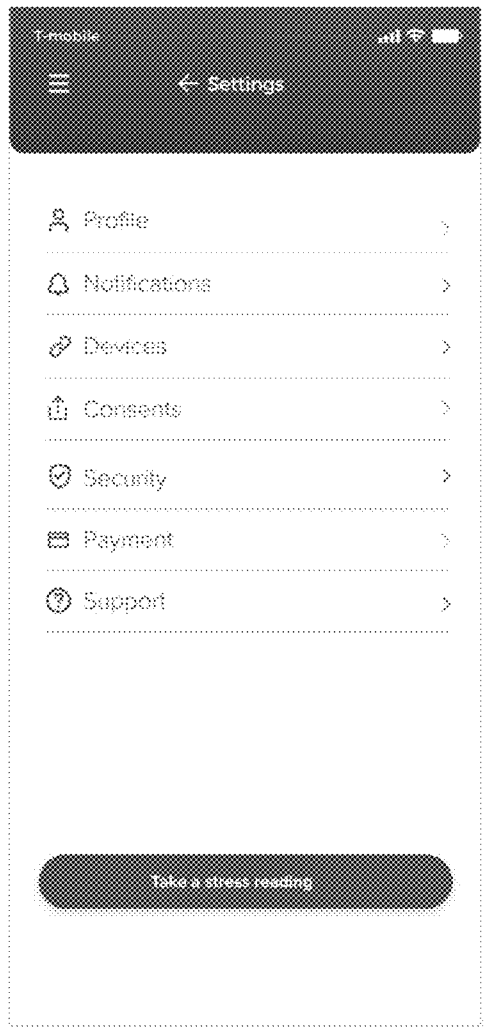

FIG. 30 is a screenshot of a graphical user interface (GUI) provided by the software application in which multiple system settings are presented.

Figure 31:
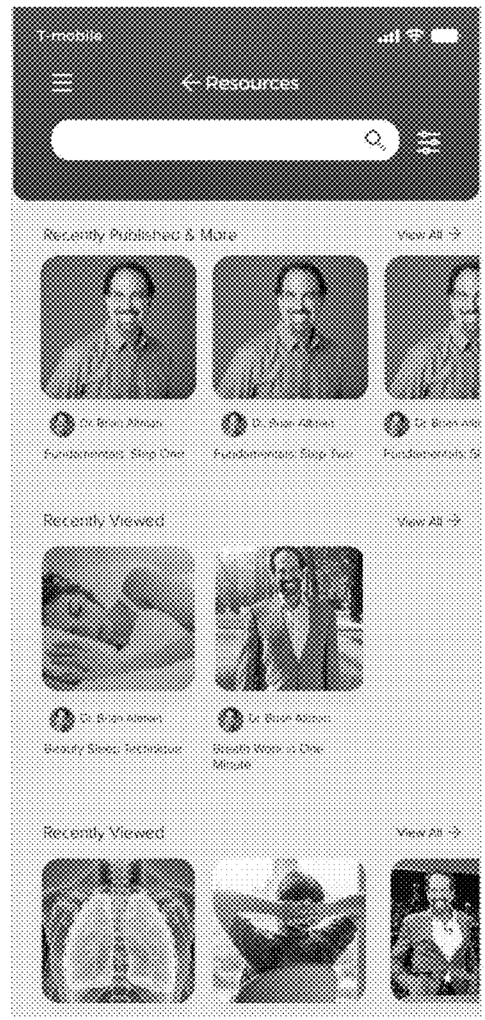

FIG. 31 is a screenshot of a graphical user interface (GUI) provided by the software application in which multiple resources for stress mitigation are presented.

Mitigation Strategies

If the subject is determined to be experiencing stress, the device (and/or system) is configured to provide the subject with one or more mitigation strategies (interventions) designed to reduce or alleviate the subject's stress. Examples of such interventions may include but are not limited to providing videos, podcasts, or the like to the subject through the device to facilitate meditation, relaxation, or the like, as well as suggestions to exercise and/or contact or visit a counselor, ingest a prescription or non-prescription medication, etc. Other examples of interventions that can be provided in accordance with the invention include having a counselor or other medical professional call or otherwise communicate with the subject in the event s/he is determined to be experiencing psychological stress.

It will be understood that the individual devices of the invention can also be part of a larger, cloud-based system that delivers services over the Internet on an as-needed basis, relying on shared computing resources rather than local servers or personal computing devices to run applications. Preferably, an application is used to configure a computer that is part of a mobile computing device, e.g., a smartphone (e.g., an Apple Iphone®, Samsung Galaxy mobile phone), laptop computer, tablet computer (e.g., an iPad®, Chromebook®, etc.) to perform methods of the invention, namely, to computationally determine from image data captured using a camera associated with (e.g., integrated as part of) the device whether one or more blood flow parameters (e.g., HRV, HR, etc.) associated or correlated with psychological stress detected in blood perfusing regions of interest in the skin of a subject, alone or together with other data correlated with acute psychological stress, indicate that the subject was experiencing acute psychological stress at the time the image data was collected. In some embodiments, an application runs in part on a mobile computing device and in part on another computer or computer network (e.g., a cloud-based computer network) linked thereto, for example, via the Internet, be it via a hardwire (e.g., Ethernet) connection or wirelessly.

The cloud-based system of the invention typically includes at least one processor, read only memory (ROM), random access memory (RAM), network interface, a mass storage device, and a database coupled together by a communications bus. The processors may be microprocessors, and the mass storage device may comprise one or more local or remote magnetic disk drives, solid-state storage devices, and/or storage devices. The mass storage device (or interconnected system comprising a plurality of such devices) and memory modules are connected to the processor(s) to allow the processor(s) to write data into and read data from the storage and memory devices. The network interface couples the system to a network, for example, the Internet. The nature of the network and of the devices that may be interposed between the system and the network determines the kind of network interface used in the system. In some embodiments, for example, the network interface may be an Ethernet interface that connects the system to a local area network, which, in turn, connects to the Internet. The network also preferably includes a cellular interface that to provide connectivity between the network and users' mobile computing devices (e.g., smartphones, laptop personal computers, tablet computers, etc.), although users can also employ desktop and other computers having a camera (e.g., a webcam) operably associated therewith. The database may be used for organizing and storing data that may be needed or desired in performing the method steps on the invention, including storing the image/video data obtained from users' cameras. In some embodiments, the processor(s) and the mass storage device are configured to perform the functions of the database.

As is known, processors are configured to read and execute program code instructions stored in machine-readable storage devices. Under control of program code, in some embodiments, the processors configure the system and/or users' corresponding app-running smartphones to perform the methods of the invention. The program code instructions may be embodied in other machine-readable storage media, such as additional hard drives, floppy diskettes, CD-ROMs, DVDs, flash memories, and similar devices. The program code can also be transmitted over a transmission medium, for example, over electrical wiring or cabling, through optical fiber, wirelessly, or by any other form of physical or wireless transmission. The transmission can take place over a dedicated link between telecommunication devices, or through a wide- or local-area network, such as the Internet, an intranet, extranet, or any other kind of public or private network.

As described above, some or all of the process steps of the invention can be performed by the system in conjunction with one or more of app-running smartphones or other personal telecommunications or computing devices having a camera, preferably a high-resolution video camera, operably associated therewith. In some embodiments, the process steps may be performed by the system alone, in which case the system will be equipped with one or more image capture devices such as a camera, or otherwise have access to images/video of a subject to be assessed. The process steps may also be performed by personal computing devices, preferably smartphones, which are capable of permanent or intermittent physical or wireless network connectivity.

The analyzed images/video can be obtained by any suitable type of camera, including webcams built into personal computers or mobile devices, video cameras for taking moving video images, digital cameras capable of taking still pictures and/or capturing continuous video streams, stereo cameras, and/or any other digital imaging device.

Various lenses, filters, and other optical devices, such as zoom lenses, wide angle lenses, minors, prisms, and the like may also be used with the image capture device to assist in capturing images/video. The image capture devices may be stationary, i.e., fixed in a particular orientation and configuration. The image capture devices (along with any of their accompanying optical devices) may also be fixed on a gimbal and be programmable in orientation and position. The image capture devices can also be capable of moving along one or more directions, such as up, down, left, and right; and/or rotate about one or more axes of rotation. The image capture device may also be capable of moving to follow or track an object, including a person, an animal, or another object in motion. In other words, the image capture device may be capable of moving about an axis of rotation in order to keep a person or object within a viewing range of the device's lens.

Although the process steps and decisions (if decision blocks are present) may be described serially herein, certain steps and/or decisions may be performed by separate elements in conjunction or in parallel, asynchronously or synchronously, in a pipelined manner, or otherwise. There is no particular requirement that the steps and decisions be performed in the same order in which this description lists them or as shown in the Figures, except where a specific order is inherently required, explicitly indicated, or is otherwise made clear from the context. Furthermore, not every illustrated step and decision block may be required in every embodiment in accordance with the concepts described in this document, while some steps and decision blocks that have not been specifically illustrated may be desirable or necessary in some embodiments in accordance with the concepts. It should be noted, however, that specific embodiments/variants/examples use the particular order(s) in which the steps and decisions (if applicable) are shown and/or described.

In various embodiments, the features, elements, and limitations of apparatus and processes described throughout this document may be present individually, or in any combination or permutation, except where the presence or absence of specific feature(s)/element(s)/limitation(s) is inherently required, explicitly indicated, or otherwise made clear from the context.

Unless the context clearly requires otherwise, throughout the description above and the appended claims, the words "comprise", "comprising", and the like are to be construed in an inclusive sense as opposed to an exclusive or exhaustive sense; that is to say, in a sense of "including, but not limited to". Words using the singular or plural number also include the plural or singular number, respectively. Additionally, the words "herein", "hereunder", "above", "below", and words of similar import refer to this application as a whole and not to any particular portions of this application. When the word "or" is used in reference to a list of two or more items, that word covers all of the following interpretations of the word: any of the items in the list; all of the items in the list; and any combination of the items in the list.

The foregoing description, for the purpose of explanation, has been described with reference to specific embodiments. However, the illustrative discussions above are not intended to be exhaustive or to limit the invention to the precise forms disclosed. Many modifications and variations are possible in view of the above descriptions. The embodiments were chosen and described in order to best explain the principles of the invention and its practical applications to thereby enable others skilled in the art to best utilize the invention and various embodiments with various modifications as are suited to the particular use contemplated. As such, the invention extends to all functionally equivalent structures, methods, and uses, such as are within the scope of the appended claims, and it is intended that the invention be limited only to the extent required by the applicable rules of law.

With regard to the appended claims, it is understood that, once issued, they represent only patentable subject matter, and any claimed process, machine, or article of manufacture according to the invention means that the subject matter satisfies all statutory requirements for patentability at the time the analysis is performed. For example, with regard to novelty, non-obviousness, or the like, if later investigation reveals that one or more claims encompass one or more embodiments that would negate novelty, non-obviousness, etc., the claim(s), being limited by definition to "patentable" embodiments, specifically exclude any unpatentable embodiment(s). Also, the claims appended hereto are to be interpreted both to provide the broadest reasonable scope, as well as to preserve their validity. Furthermore, if one or more of the statutory requirements for patentability are amended or if the standards change for assessing whether a particular statutory requirement for patentability is satisfied from the time this application is filed or issues as a patent to a time the validity of one or more of the appended claims is questioned, the claims are to be interpreted in a way that, to the maximum extent then permissible, (1) preserves their validity and (2) provides the broadest reasonable interpretation under the circumstances.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular system, device or component thereof to the teachings of the disclosure without departing from the essential scope thereof. Therefore, it is intended that the disclosure not be limited to the particular embodiments disclosed for carrying out this disclosure, but that the disclosure will include all embodiments falling within the scope of the appended claims. Moreover, the use of the terms first, second, etc. do not denote any order or importance, but rather the terms first, second, etc. are used to distinguish one element from another.

Although certain specific embodiments are described above for instructional purposes, the teachings of this patent document have general applicability and are not limited to the specific embodiments described above. For additional information on how to obtain heart rate characteristics based on an image obtained via a camera, see: U.S. Pat. No. 10,335,045 to Sebe et al., and U.S. Pat. Publ. No. 2017/0007137 to Hong et al., each of which is incorporated herein by reference in its entirety. Accordingly, various modifications, adaptations, and combinations of various features of the described embodiments can be practiced without departing from the scope of the embodiments as set forth in the claims.

What is claimed is:

1. A method comprising:
acquiring an image of a user;
recognizing a region of interest (ROI) in the image, wherein the ROI is an area of skin on the user's face that is perfused with blood;
analyzing the ROI to generate statistics, wherein the statistics include heart rate variability (HRV), wherein analyzing the ROI involves decomposing the ROI data into a plurality of color channels and applying one or more spatial filters to the color channels;
determining a level of stress experienced by the user based on the statistics;
providing one or more interventions to the user to reduce the level of stress, wherein interventions provided to the user are filtered based on effectiveness ratings provided by the user;
prompting a user to rate effectiveness of each of the one or more interventions; and
maintaining a mitigation database that is updated with user effectiveness ratings for each of the one or more interventions.

2. The method of claim 1, wherein the operation of recognizing comprises identifying a region of the user's skin that is highly perfused with blood as the ROI.

3. The method of claim 1, further comprising conveying the level of stress to the user.

4. The method of claim 1, further comprising conveying the level of stress to a third party.

5. The method of claim 1, wherein the one or more interventions comprise at least one of video, music, a document, or meditation.

6. The method of claim 1, wherein the one or more interventions comprise advising the user to contact a counselor.

7. The method of claim 1, wherein the operation of determining the level of stress comprises determining the level of stress experienced by the user based on the statistics and aggregated data about the user.

8. The method of claim 7, wherein the operation of determining the level of stress comprises determining the level of stress experienced by the user based on the statistics, the aggregated data about the user, and user input in response to questions.

9. The method of claim 8, further comprising:
individually weighting the statistics, the aggregated data, and the user input to generate weighted parameters; and
accumulating the weighted parameters to determine the stress level.

10. An apparatus comprising:
an image sensor that acquires an image of a user;
a mitigation database that stores one or more stress mitigation strategies; and
a processor configured to perform operations of:
recognizing a region of interest (ROI) in the image, wherein the ROI is an area of skin on the user's face that is perfused with blood;
analyzing the ROI to generate statistics, wherein the statistics include heart rate variability (HRV), wherein analyzing the ROI involves decomposing the ROI data into a plurality of color channels and applying one or more spatial filters to the color channels;
determining a level of stress experienced by the user based on the statistics;
presenting the one or more stress mitigation strategies to the user to reduce the level of stress, wherein stress mitigation strategies presented to the user are filtered based on effectiveness ratings provided by the user;
prompting a user to rate effectiveness of each of the one or more stress mitigation strategies; and
maintaining the mitigation database to be updated with user effectiveness ratings for each of the one or more stress mitigation strategies.

11. The apparatus of claim 10, wherein the operation of recognizing comprises identifying a region of the user's skin that is highly perfused with blood as the ROI.

12. The apparatus of claim 10, wherein the processor is further configured to convey the level of stress to the user.

13. The apparatus of claim 10, wherein the processor is further configured to convey the level of stress to a third party.

14. The apparatus of claim 10, wherein the one or more stress mitigation strategies comprise at least one of video, music, a document, or meditation.

15. The method of claim 1, wherein the analyzing of the ROI involves filtering image data to predict timing of heartbeat-based parameters.

16. The method of claim 1, wherein more effective interventions are presented before less effective interventions, wherein effectiveness is determined by user feedback, wherein the user feedback is obtained by prompting a user to rate the effectiveness of an intervention.

17. The apparatus of claim 10, wherein the analyzing of the ROI involves filtering image data to predict timing of heartbeat-based parameters.

18. The apparatus of claim 10, wherein more effective stress mitigation strategies are presented before less effective stress mitigation strategies, wherein effectiveness is determined by user feedback, wherein the user feedback is obtained by prompting a user to rate the effectiveness of a stress mitigation strategy.

* * * * *